(12) United States Patent
Galloway, Jr. et al.

(10) Patent No.: US 7,072,707 B2
(45) Date of Patent: Jul. 4, 2006

(54) METHOD AND APPARATUS FOR COLLECTING AND PROCESSING PHYSICAL SPACE DATA FOR USE WHILE PERFORMING IMAGE-GUIDED SURGERY

(75) Inventors: Robert L. Galloway, Jr., Nashville, TN (US); William C. Chapman, Nashville, TN (US); James D. Stefansic, Nashville, TN (US); Alan J. Herline, Nashville, TN (US); Michael I. Miga, Franklin, TN (US); David M. Cash, Nashville, TN (US); Tuhin K. Sinha, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 156 days.

(21) Appl. No.: 10/418,187

(22) Filed: Apr. 16, 2003

(65) Prior Publication Data

US 2004/0019274 A1    Jan. 29, 2004

Related U.S. Application Data

(63) Continuation-in-part of application No. 09/894,732, filed on Jun. 27, 2001, now Pat. No. 6,584,339.

(51) Int. Cl.
*A61B 5/05* (2006.01)

(52) U.S. Cl. ............ 600/424; 600/407; 600/423; 600/434; 600/476

(58) Field of Classification Search ............ 600/407, 600/410, 411, 415, 416, 417, 420, 425, 427, 600/429, 436, 437, 442, 443, 473, 476
See application file for complete search history.

(56) References Cited

U.S. PATENT DOCUMENTS 4,334,221 A    6/1982    Rosenhagen et al. ........ 340/825

5,383,454 A    1/1995    Bucholz
5,647,361 A    7/1997    Damadian (Continued)

FOREIGN PATENT DOCUMENTS

EP    0 921 657    12/2003

(Continued)

OTHER PUBLICATIONS

Stefansic et al., "Interactive, Image-Guided Hepatic Surgery," Part of the SPIE Conference on Image Display, pp. 241-251, (Feb., 1999).

(Continued)

*Primary Examiner*—Brian L. Casler
(74) *Attorney, Agent, or Firm*—Akin Gump Strauss Hauer & Feld, LLP

(57) ABSTRACT

A method and apparatus for collecting and processing physical space data used while performing image-guided surgery is disclosed. Physical space data is collected by probing physical surface points of surgically exposed tissue. The physical space data provides three-dimensional (3-D) coordinates for each of the physical surface points. Based on the physical space data collected, point-based registrations used to indicate surgical position in both image space and physical space are determined. In one embodiment, the surface of surgically exposed tissue of a living patient is illuminated with laser light. Light reflected from the illuminated surface of the exposed tissue is received and analyzed. In another embodiment, one or more magnetic fields of known shape and size are established in the proximity of the exposed tissue. Data associated with the strength of the magnetic fields is acquired and analyzed.

13 Claims, 16 Drawing Sheets

U.S. PATENT DOCUMENTS

| | | | |
|---|---|---|---|
| 5,663,716 A | 9/1997 | Miwa et al. | 340/825 |
| D387,427 S | 12/1997 | Bucholz et al. | |
| 5,817,105 A | 10/1998 | Van Der Brug | |
| 5,851,183 A | 12/1998 | Bucholz | |
| 5,870,381 A | 2/1999 | Kawasaki et al. | 370/213 |
| 5,871,445 A | 2/1999 | Bucholz | |
| 5,891,034 A | 4/1999 | Bucholz | |
| 5,970,499 A | 10/1999 | Smith et al. | |
| 5,980,535 A | 11/1999 | Barnett et al. | |
| 5,982,742 A | 11/1999 | Leung et al. | 370/213 |
| 5,987,960 A | 11/1999 | Messner et al. | |
| 5,999,840 A * | 12/1999 | Grimson et al. | 600/424 |
| 6,013,087 A | 1/2000 | Adams et al. | |
| D420,132 S | 2/2000 | Bucholz et al. | |
| 6,021,343 A | 2/2000 | Foley et al. | |
| 6,038,467 A | 3/2000 | De Bliek et al. | |
| D422,706 S | 4/2000 | Bucholz et al. | |
| 6,045,532 A | 4/2000 | Eggers et al. | |
| 6,066,123 A | 5/2000 | Li et al. | |
| 6,066,134 A | 5/2000 | Eggers et al. | |
| 6,076,008 A | 6/2000 | Bucholz | |
| 6,112,113 A | 8/2000 | Van Der Brug et al. | |
| 6,135,946 A | 10/2000 | Konen et al. | |
| 6,161,033 A | 12/2000 | Kuhn | |
| 6,167,292 A | 12/2000 | Badano et al. | |
| 6,187,018 B1 | 2/2001 | Sanjay-Gopal et al. | |
| 6,195,577 B1 | 2/2001 | Truwit et al. | |
| 6,236,875 B1 | 5/2001 | Bucholz et al. | |
| 6,259,943 B1 | 7/2001 | Cosman et al. | |
| 6,374,135 B1 | 4/2002 | Bucholz | |
| 6,390,982 B1 * | 5/2002 | Bova et al. | 600/443 |
| 6,490,475 B1 | 12/2002 | Seeley et al. | |
| 6,584,339 B1 * | 6/2003 | Galloway et al. | 600/426 |

FOREIGN PATENT DOCUMENTS

| | | |
|---|---|---|
| WO | 98/44472 | 8/1998 |

OTHER PUBLICATIONS

Herline et al., "Surface Registration For Use In Interactive, Image-Guided Liver Surgery," Presented at the Second International Medical Image Computing and Computer-Assisted Intervention (MICCA) Conference, 16 pp., (Sep. 1999).

Stefansic et al., "Registration Of Physical Space To Laparoscopic Image Space For Use In Minimally Invasive Hepatic Surgery," IEEE Transactions on Medical Imaging, vol. 19, No. 10, pp. 1012-1023, (Oct. 2000).

Beasley et al., "Implementation And Incorporation Of Liver 3-D Surface Renderings Into Interactive, Image-Guided Hepatic Surgery," Proc. of SPIE vol. 3976, Image Display and Visualization, pp. 282-289, (Feb. 2000).

Galloway et al., "Task-Oriented Asymmetric Multiprocessing For Interactive Image-Guided Surgery," Parallel Computing 24, pp. 1323-1343, (1998).

Onocology News International, "Radiofrequency Ablation Used To Treat Liver Metastases," vol. 8, No. 10, (Oct. 1999).

Patterson, Sunita, "Promising Radio Frequency Treatment—New Option For Patients With Unresectable Liver Tumors," OncoLog, vol. 43, No. 3 (Mar. 1998).

* cited by examiner

| Calibration Trial | Samples | Tracking error, mm |
|---|---|---|
| 1 | 36 | 1.25 ± 0.51 (2.35) |
| 2 | 36 | 0.95 ± 0.45 (2.27) |
| 3 | 36 | 1.58 ± 0.97 (4.34) |
| 4 | 36 | 1.01 ± 0.59 (2.51) |
| 5 | 36 | 2.12 ± 0.95 (3.68) |
| 6 | 18 | 1.74 ± 0.62 (2.62) |
| 7 | 18 | 1.46 ± 0.60 (2.32) |
| 8 | 18 | 1.42 ± 0.55 (2.15) |
| OVERALL | 234 | 1.43 ± 0.79 (4.34) |

*Fig. 11*

| Ridge | Initial FRE | Trials | Failures | Translation range, mm | Successful Rotation range, degrees | Average distance from mean success position, mm |
|---|---|---|---|---|---|---|
| Incomplete | 16.2 | 396 | 30 | X: (-40, +40)<br>Y: (-40, +36)<br>Z: (-40, +40) | X: (-25, +14)<br>Y: (-25, +25)<br>Z: (-10, +25) | 0.24 ± 0.06 |
| Complete | 19.1 | 455 | 1 | X: (-50, +50)<br>Y: (-50, +50)<br>Z: (-50, +50) | X: (-25, +24)<br>Y: (-25, +25)<br>Z: (-25, +25) | 1.3 ± 0.2 |

*Fig. 13*

| Tumor | Initial error, mm | Rigid Error, mm | % change | Rigid + Deformation error, mm | % change from initial | % change from rigid |
|---|---|---|---|---|---|---|
| 1 | 46.8 | 3.8 | -91.8% | 1.9 | -4.1 | -50.0 |
| 2 | 33.7 | 3.7 | -89.0% | 2.4 | -3.9 | -35.1 |
| 3 | 11.5 | 6.4 | -44.0% | 5.0 | -13.0 | -23.2 |
| 4 | 6.0 | 6.2 | 4.1% | 4.4 | -29.8 | -28.7 |
| 5 | 3.7 | 6.6 | 80.7% | 6.5 | -4.4 | -2.4 |
| 6 | 4.7 | 7.7 | 65.7% | 7.8 | 2.0 | 1.2 |
| MEAN | 17.7 | 5.8 | -67.2 | 4.7 | -6.2 | -18.9 |

*Fig. 15*

METHOD AND APPARATUS FOR COLLECTING AND PROCESSING PHYSICAL SPACE DATA FOR USE WHILE PERFORMING IMAGE-GUIDED SURGERY

CROSS-REFERENCE TO RELATED APPLICATIONS

This application is a continuation-in-part of U.S. patent application Ser. No. 09/894,732, filed Jun. 27, 2001, now a U.S. Pat. No. 6,584,339 entitled "Method and Apparatus for Collecting and Processing Physical Space Data for Use While Performing Image-Guided Surgery," which is incorporated herein by reference in its entirety.

STATEMENT REGARDING FEDERALLY SPONSORED RESEARCH OR DEVELOPMENT

This work was supported in part by grants from the National Institutes of Health (NIH) and the National Science Foundation (NSF) (NIH grants NIGMS GM52798, NRSA #1 F32 DK 09671-01 SB and R21 CA 91352-01; and NSF grants BES-9703714) and the U.S. Government may therefore have certain rights in this invention.

BACKGROUND OF THE INVENTION

1. Field of the Invention

The present invention relates to using image-guided surgery techniques to collect data to insure accurate tracking of an ablation device.

2. Background Information

For over fifty years, diagnostic images have been used for surgical guidance, especially in the field of neurosurgery. Image-guided surgery implements two fundamental ideas: first, the concept of an image-space to physical-space mapping or registration, and second, the use of an extracranial device for accurate surgical guidance without direct visualization. Such ideas gave birth to stereotactic neurosurgery, a technique for locating targets of surgical interest within the brain relative to an external frame of reference. This is traditionally defined as the temporary attachment of a mechanical frame to the skull or scalp in order to define a 3-D frame space around a patient. With the advent of computed tomography (CT), the coordinates of a target (i.e. tumor) in image space could be assigned coordinates in frame space if the CT images are obtained with the attached frame. Unfortunately, frames are uncomfortable to patients, must be applied prior to imaging, and are cumbersome in the imaging environment and the operating room.

These factors led to the development of frameless stereotactic surgical systems, or interactive, image-guided surgery (IIGS) systems. In traditional IIGS systems, present surgical position is tracked during an operation and displayed on pre-operatively obtained tomographic images. As the surgeon changes the current surgical position, displayed images are updated in real time. In one of the earliest IIGS systems, physical space surgical position was determined using articulated arms. The position of an articulated pointer was calculated using a personal computer (PC) and overlayed on tomographic images. Magnetic resonance images (MRI) and CT negative films are scanned into the computer and displayed as images on a video interface. Other early image-guided surgical systems also used electromechanical 3-D coordinate digitizers to indicate present surgical position on various representations of patient data, including 2-D transverse, coronal and sagittal CT or MRI slices, and on image renderings of the physical object surface. Since it was necessary to have computers capable of managing large volumes of image information (>100 Mbytes) and updating the display quickly, most early IIGS systems are were developed with VME bus devices running UNIX.

Early IIGS systems were developed on PCs using multiple processors. In a task-oriented asymmetric multiprocessing (TOAM) system developed in 32 bit extended DOS, discrete tasks such as physical space localization, data fetching, and display were conducted asynchronously on specialized processors which communicated with inexpensive, general purpose processors that worked as loaders and schedulers. For physical space localization, several articulated arms with six degrees of freedom were first developed. These cumbersome arm devices were eventually replaced with lightweight cylindrical pen-like probes which could be tracked more easily in the operating room using an optical triangulation system. The spatial location of the guidance instrument was determined using a collection of discrete processors which continually update the physical space location. This location was then passed to the central processor where it was mapped into image space. Once the image space map was complete, the appropriate tomographic slices were selected and displayed. Because this system was designed before the advent of large memory availability, image display relied heavily on hardware manipulation using disk controllers to load images directly from the hard drive. Control of the bus was passed from the main processor to the disk drive controller, where the correct image was fetched and sent to the display processor.

With the continuing increase in performance to price, processes which could only be performed on workstation class machines are now routinely performed on PCs. As the PC hardware evolved, however, it became apparent that DOS-based systems would not have the continuing support of hardware vendors.

Because of these considerations, a need for an operating room image-oriented navigation system (ORION) emerged. ORION was developed in Windows NT using MS Visual C++ 6.0 with the Win32 API. Not only was this system designed to be faster than the previous one, but it was not necessary to redesign the software with each hardware advance. Components of the system were developed as dynamic link libraries (DLLs), so that new technology could be incorporated into the system without a complete software rewrite. The system is also somewhat portable. It runs adequately on any PC with a 200 MHz or higher Pentium processor and 128 MB of memory which also has the appropriate video card and 3-D localizer hardware and software.

When designing an image-guided surgical system, it is critical that the precise location of an ablative instrument used to perform image-guided surgery be determined on a continuous basis (e.g., update rates approaching 30 frames per second). Further, in an effort to insure the utmost in precision, an ablation zone of the ablative instrument, the tissue being operated on, and a particular portion of the tissue to be resected or ablated during surgery must also be continuously and accurately tracked.

What is needed is a method and apparatus for collecting and processing physical space data for use while performing image-guided surgery, such that tumors and lesions in the tissue of a living patient can be accurately located, and resected or ablated with a precisely tracked ablative instrument. The present invention fulfills such a need.

BRIEF SUMMARY OF THE INVENTION

In interactive, image-guided surgery, current physical space position in the operating room is displayed on various sets of medical images used for surgical navigation. The present invention is a PC-based surgical guidance system which synchronously displays surgical position on up to four image sets and updates them in real time. There are three essential components and techniques which have been developed for this system: 1) accurately tracked ablative instruments, 2) accurate registration techniques to map physical space to image space, and 3) methods and apparatus to display and update the image sets on a computer monitor. For each of these components, a set of dynamic link libraries has been developed in MS Visual C++ 6.0 supporting various hardware tools and software techniques. Surgical (i.e., ablative) instruments are tracked in physical space using an active optical tracking system. Several different registration algorithms were developed with a library of robust math kernel functions, and the accuracy of all registration techniques have been thoroughly investigated. The present invention was developed using the Win32 API for windows management and tomographic visualization, a frame grabber for live video capture, and OpenGL for visualization of surface renderings. This current implementation of the present invention can be used for several surgical procedures, including open and minimally invasive liver surgery.

In a method according to the present invention, physical space data is collected and processed for use while performing image-guided surgery. Tissue of a living patient is surgically exposed. Physical space data is then collected by (i) illuminating the surface of the exposed tissue with laser light, (ii) receiving light reflected from the illuminated surface of the exposed tissue, and (iii) performing an analysis on the reflected light, the physical space data providing three-dimensional (3-D) coordinates for each of the physical surface points. Based on the physical space data collected, point-based registrations used to indicate surgical position in both image space and physical space are determined. The registrations are used to map into image space, image data describing the physical space of an ablative instrument used to perform the image-guided surgery, an ablation zone of the instrument, the tissue, and a particular portion of the tissue to be resected or ablated.

The tissue may be the patient's liver and the particular portion of tissue to be resected or ablated may be a hepatic metastatic tumor.

Prior to surgery, tissue of the patient may be scanned to acquire, store and process a 3-D description of the organ or structure of interest (e.g., a 3-D reference). A triangularized mesh may be created based on the scanned tissue. The volumetric center of a particular portion of the tissue to be resected or ablated during the surgery may be determined, wherein an algorithm using the triangularized mesh and the collected physical space data may be implemented to determine the point-based registrations. The algorithm may be an iterative closest point (ICP) registration algorithm.

The scanning of the tissue may be performed by one of a computerized tomography (CT) scanner, a magnetic resonance imaging (MRI) scanner and a positron emission tomography (PET) scanner.

In an apparatus according to the present invention, physical space data is collected and processed for use while performing image-guided surgery. The apparatus comprises a laser scanner, an ablative instrument and an image data processor. The laser scanner collects physical space data by (i) illuminating the surface of surgically exposed tissue of a living patient with laser light, (ii) receiving light reflected from the illuminated surface of the exposed tissue, and (iii) performing an analysis on the reflected light. The physical space data provides three-dimensional (3-D) coordinates for each of the physical surface points. The ablative instrument may resect or ablate a particular portion of the exposed tissue.

The image data processor comprises a computer-readable medium holding computer-executable instructions which, based on the physical space data collected by the probe instrument, determine point-based registrations used to indicate surgical position in both image space and physical space. Using the point-based registrations to map into image space, image data describing the physical space of an ablative instrument used to perform the image-guided surgery, an ablation zone of the ablative instrument, the tissue, and a particular portion of the tissue to be resected or ablated.

In an alternative embodiment, physical space data is collected by (i) establishing one or more magnetic fields of known shape and size in the proximity of the exposed tissue, (ii) acquiring data associated with the strength of the magnetic fields, and (iii) performing an analysis on the acquired data

BRIEF DESCRIPTION OF THE SEVERAL VIEWS OF THE DRAWINGS

The following detailed description of preferred embodiments of the present invention would be better understood when read in conjunction with the appended drawings. For the purpose of illustrating the present invention, there are shown in the drawings embodiments which are presently preferred. However, the present invention is not limited to the precise arrangements and instrumentalities shown. In the drawings:

FIG. 11 shows experimental tracking results of a tracking calibration procedure used with a laser scanner;

FIG. 13 shows experimental results of a sensitivity study using a laser scanner;

FIG. 15 shows results from deformation studies; and

DETAILED DESCRIPTION OF THE INVENTION

Figure 1:
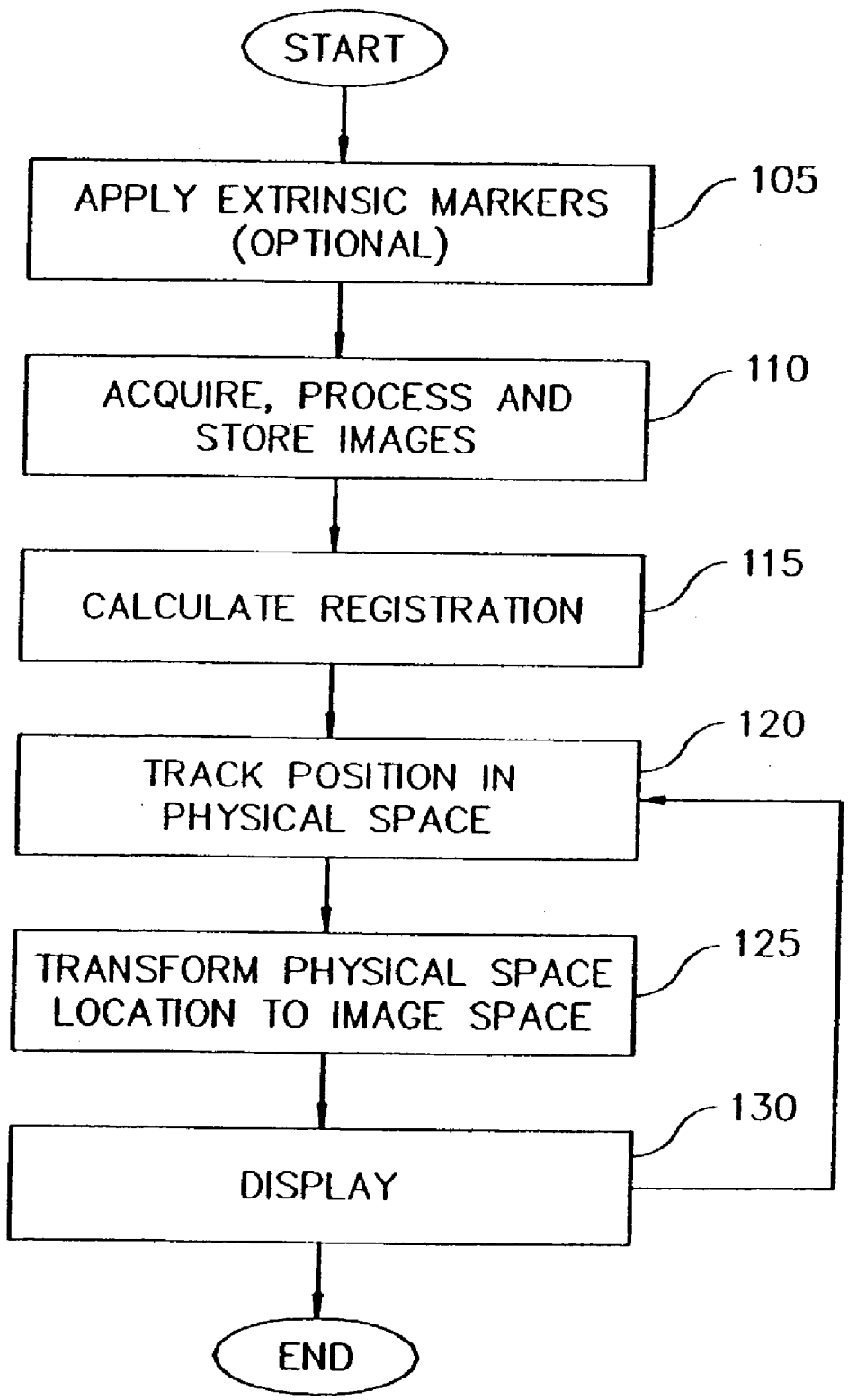
FIG. 1 shows a general flow chart in accordance with the present invention.

FIG. 1 shows some of the major events involved in preparing for and performing IIGS. In step 105, it is determined if any extrinsic markers will be attached to the patient. These makers, or fiducials, are designed to be imaged and then localized in both image space and physical space for use in a point-based registration algorithm. Appropriate image volumes for a patient are then acquired, stored and processed (step 110). Most image volumes are acquired as a set of slices, 256×256 or 512×512 pixels per slice at 2 bytes per pixel with 20–200 images per volume. These images are acquired on a computerized tomography (CT) scanner, a magnetic resonance imaging (MRI) scanner or a positron emission tomography (PET) scanner. Images are typically transferred from PACS servers in radiology to image-guided surgical computers, where they are processed for display before surgery if necessary. Transverse, sagittal, or coronal tomographic slices require minor processing before display. In order to visualize surface renderings, a triangulated surface can be created from the volume and displayed. These triangulated surfaces can also be used in registration algorithms to map a physical surface to an image surface.

Once the surgeon has prepared and positioned the patient for surgery, it is necessary to register or map patient or physical space to image space before images can be used interactively (step 115). Physical space data is collected using an instrument whose position is tracked in the operating room. For point-based registrations, corresponding points that can be localized accurately in both image space and physical space are used to create the mapping. These can include extrinsic fiducials that were attached to the patient before imaging or intrinsic fiducials which include anatomic landmarks visible in both physical and image space. For surface-based registrations, a surface of physical space points is collected and mapped onto a triangulated surface. After the accuracy of the registration is assessed, the tracked instrument is moved in physical space and the corresponding position in image space is displayed (steps 120, 125 and 130) and used as a guide during the surgical procedure.

In order to carry out the tasks of determining the location of a tracked probe in space, registering that position into image space, and displaying the appropriate image or images on a computer screen, three divisions of run-time dynamic link libraries (DLLs) were initially developed for our system. The first is a localizer division, which is responsible for determining current surgical position based on the location of an instrument in space. The second is a registration division, which calculates accurate mappings between image space and physical space. The third is a display division, which displays various types of medical images on the computer screen. By separating the system into several DLL divisions, the present invention allows for modularity. Depending on a particular surgical case, for instance, a surgeon may choose one type of localizer, one or more types of displays, and one or more types of registration to indicate surgical position on the images.

Because an image-guided surgical system is, by definition, used in surgery by surgeons and surgical staff, the present invention has an intuitive interface and display to minimize the potential for distraction. Using a simple push-button interface, a patient is selected from the database, physical space data is collected, and a registration between physical space and image space is calculated. Images are then selected and displayed in one of four quadrants on the screen and updated as surgical position changes.

A surgeon can use the present invention for guidance in extremely delicate procedures, such as removing a tumor from a sensitive region of the brain or resect multiple lesions in regions of the liver near major blood vessels. It is important that current surgical position displayed on medical images be as close to actual surgical position as possible. It is also imperative that the images are updated quickly, since a surgeon may change his or her current location rapidly in order to gather spatial information about a certain structure and its surroundings. Accordingly, there are two performance goals in the development of the present invention: accuracy and speed. It is necessary to develop accurate, automatic registration algorithms to map physical space to image space. These algorithms should also be computationally efficient since time constraints are always a concern in surgical applications. It is also important to develop accurately tracked instruments to indicate current surgical position in physical space. Once the registration is calculated and instrument location is mapped into image space, it is necessary to update the images as fast as possible, since surgeons are sensitive to display speed. One of the worst possible scenarios would be for the surgeon to move the probe and make a decision based on the current display, only to find that the display indicated a previous position. A true image-guided surgical system should update images in real time at 30 Hz as surgical position changes.

Figure 2:
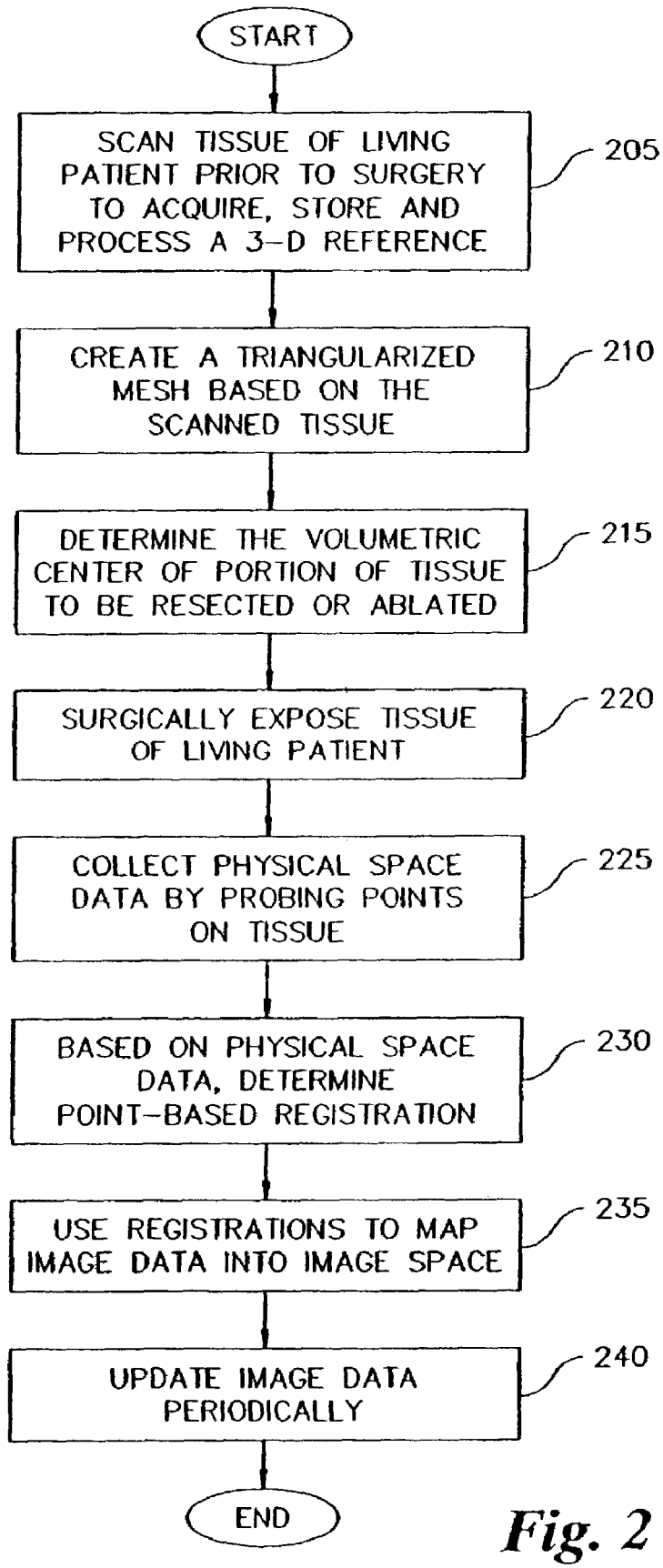
FIG. 2 shows a detailed flow chart illustrating how collected and processed physical space data is used to perform image-guided surgery in accordance with the present invention.

The present invention collects and processes physical space data for use while performing image-guided surgery, as illustrated in the flow chart of FIG. 2. Prior to surgery, tissue of the patient is scanned to acquire, store and process a 3-D reference (step 205). A triangularized mesh is then created based on the scanned tissue (step 210). The volumetric center of a particular portion of the tissue to be resected or ablated during the surgery is determined, wherein an algorithm using the triangularized mesh and the collected physical space data may be implemented to determine the point-based registrations (step 215). The algorithm may be a Besl and Mackay iterative closest point (ICP) registration algorithm.

Tissue of a living patient is then surgically exposed (step 220). Physical space data is then collected by probing a plurality of physical surface points of the exposed tissue, the physical space data providing three-dimensional (3-D) coordinates for each of the physical surface points (step 225). Based on the physical space data collected, point-based registrations used to indicate surgical position in both image space and physical space are determined (step 230). The registrations are used to map into image space, image data describing the physical space of an ablative instrument used to perform the image-guided surgery, an ablation zone of the instrument, the tissue, and a particular portion of the tissue to be resected or ablated (step 235). The image data is updated on a periodic basis (step 240).

Figure 3:
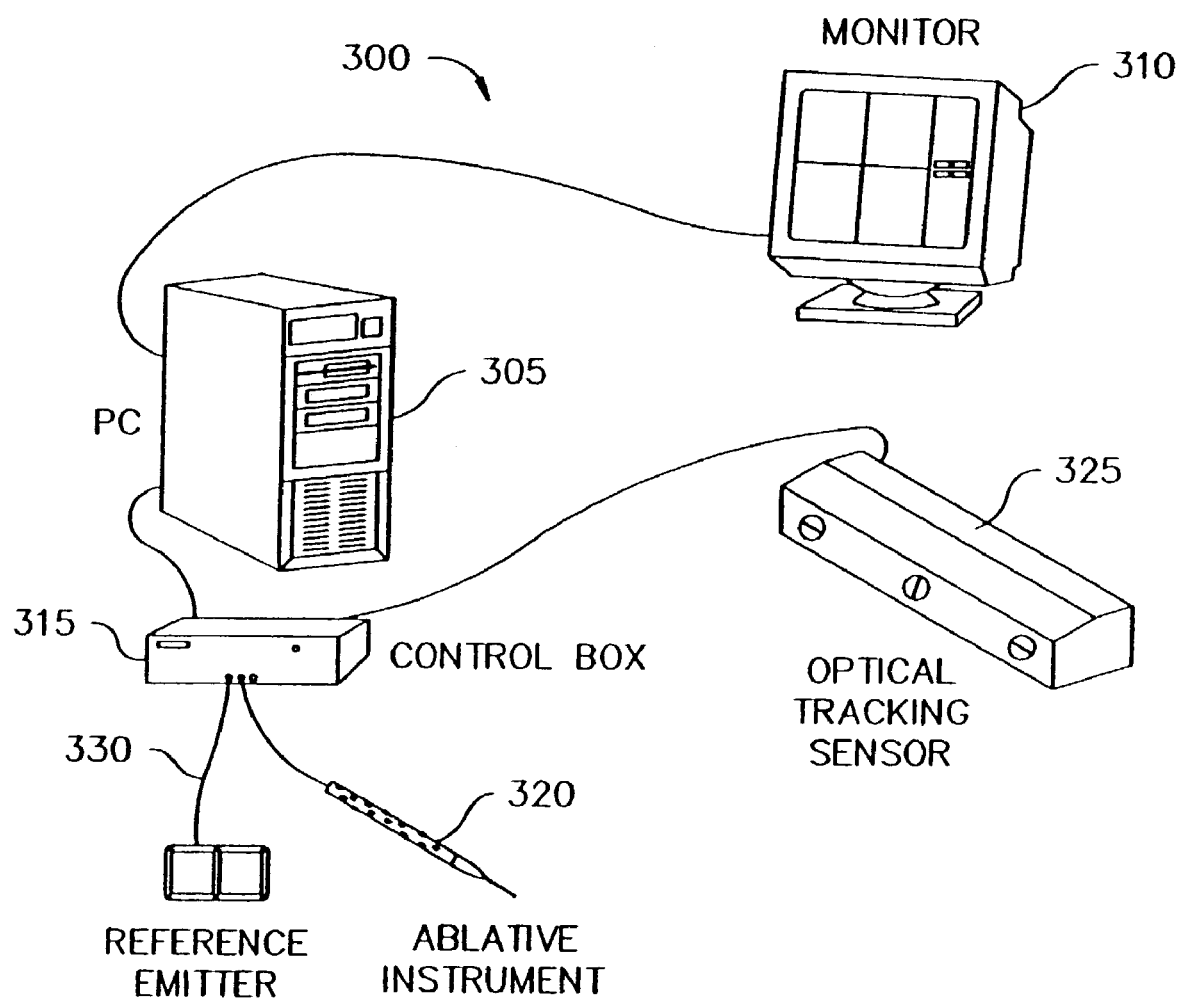
FIG. 3 shows the hardware system configuration of the present invention.

FIG. 3 shows the hardware system configuration 300 of the present invention. ORION was developed in Windows NT and is currently running on a 400 MHz processor Micron PC (an image data processor) 305 with 256 MB of memory and a display monitor 310. The display mode is 1280×1024 mode. This computer also contains two specialized cards. The VigraVision-PCI card (VisiCom Inc., Burlington, Vt.) is a combination color frame grabber and accelerated SVGA display controller which is capable of displaying NTSC video images in real time. An ISA high-speed serial port card communicates with the optical localization probe 320 via control box 315. Additional hardware for implementing the present invention include an optical tracking sensor 325, optical localization probe(s) 320, and an optical reference emitter 330.

Other paradigms for indicating surgical position could be used, including articulated arms. One preferred localization tool for use with the present invention is the Optotrak 3020 (Northern Digital Inc., Waterloo, Ontario). The optical tracking sensor 325 contains three cylindrical lenses which receive light from sequentially strobed infrared light-emitting diodes (IREDs). Triangulation is used to find each IRED relative to the position of the optical tracking sensor 325.

In order for the position and orientation of ablative instrument 320 to be measured by the optical tracking sensor 325, the ablative instrument must have a handle (rigid body) with multiple IREDs distributed over the surface of a handle of the ablative instrument 320 so that at least three IREDs are visible in all of the appropriate orientations of the ablative instrument 320. If three or more IREDs attached to the handle of the ablative instrument 320 are detected by the lenses of the optical tracking sensor 325, the tip and ablation zone of the ablative instrument 320 can be accurately localized in physical space without placing constraints on how the ablative instrument 320 needs to be handled by the surgeon.

The typical ablative instrument 320 used in neurosurgical applications has 24 IREDs which spiral around the instrument's handle. It is appropriate for use as a surgical pointer because it is light, easily directed and is extremely accurate with a tip location error of 0.35 mm in 3-D space. For endoscopic applications, a special rigid body was created for ablative instrument 320 which is more sensitive to roll for more complex manipulations. This 24 IRED "ovoid structure" attached to the endoscope weighs less than 200 g (adding less than 10% to the weight of a typical endoscope). The tip of the endoscope may be tracked with an accuracy of approximately 1.2 mm. An optically tracked radiofrequency probe is placed within the center of tumors, where it is used to microwave or heat-kill lesions. The present invention is able to track the tip of this device with an accuracy of 3.0 mm.

For surgical applications using the present invention, an ablative instrument 320 is used which not only defines a coordinate system in physical space but also preserves the registration if the patient is moved. The optical tracking sensor 325 can localize both the ablative instrument 320 and the reference emitter 330 in sensor unit space. By mapping the position of the ablative instrument 320 into the space defined by the position and orientation of the reference emitter 330, the location of the optical tracking sensor 325 drops out of the equations. The optical tracking sensor 325 can be flexibly placed before surgery and moved during the procedure to accommodate any surgical requirements.

All of the image-guided surgical software in accordance with the present invention was written using Visual C++ 6.0 in Windows NT 4.0. Because the Win32 API offers the greatest versatility in exploiting the features of Windows, this interface was chosen to create and manage the windows created in the system.

The present invention incorporates an executable program of a software system which contains the main entry point to the Windows program. Windows NT passes all user input to programs in the form of messages. Thus, the present invention implements a message pump that receives and dispatches these messages to the appropriate message handler(s). At startup, the present invention is responsible for initializing the image-guided surgery system. This task involves creating and managing the four 512×512 child windows used for image display, saving log information with the time and date the system is run, and loading the dynamic link libraries (DLLs). After initialization, the message pump in the present invention is responsible for receiving and dispatching any messages in the queue. If no messages are present, it sends information concerning the current position of the localized instrument(s) to the child windows.

Figure 4:
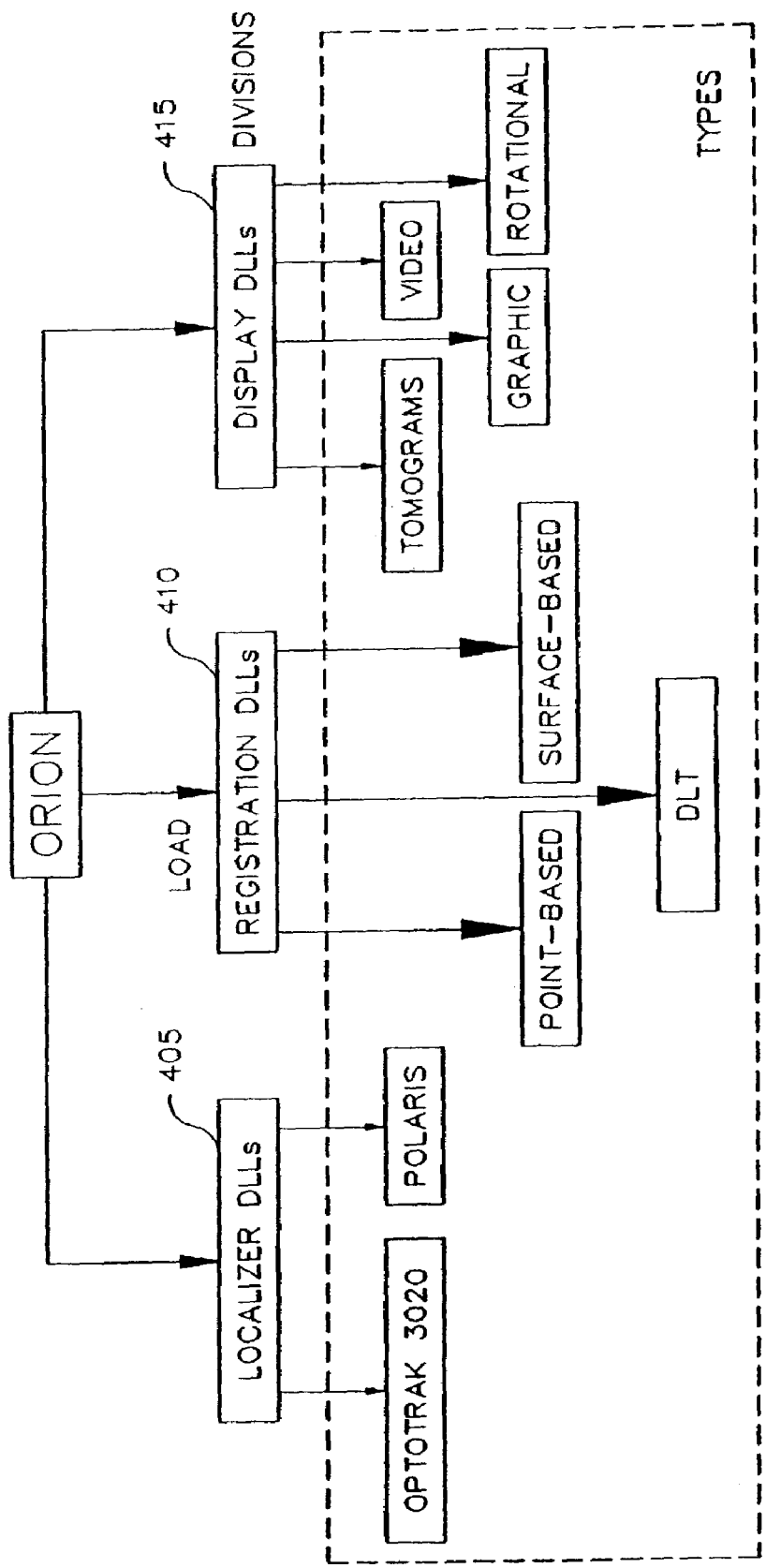
FIG. 4 shows the basic software architecture of the present invention, including the three divisions of run-time dynamic link libraries.

FIG. 4 shows the basic software architecture of the present invention, including the three divisions of run-time dynamic link libraries. For each of the three divisions, a core set of functions and structures define an interface to the DLLs. The interface represents the functionality that is required to interoperate with the present invention. Any additional functionality present within the DLL is expected to be specific to that individual DLL and not visible to the present invention. There are two functions that are common to all of the DLL interfaces, one which can be called by the present invention to receive a message related to the most recent error that occurred within the library, and another which is called to receive the identification tag for a particular type of DLL. A brief description of DLL division structure is included in the sections below, along with details about the development of particular types within a division.

The localizer division 405 consists of all the DLLs developed to track the position of instruments in physical space. The DLL interface for this division defines a common communication mechanism to various hardware devices which typically rely on vendor-supplied custom APIs for device communication. The task of implementing a localizer DLL is therefore largely a matter of grouping the API functions of the vendor into the required localizer interface functions, and ensuring correct data type conversion and error handling. A single localizer DLL is selected at startup, and all communications are performed through the interface.

Currently, localizer DLL 405 is written for the Optotrak 3020 system described previously using the Northern Digital software libraries. Several instruments can be tracked in space at once, if necessary. A function in the DLL returns 4×4 matrices that indicate the position and orientation of the optically tracked instrument(s). If either the tracked instrument(s) or the reference rigid body are blocked from the camera view or are unable to be localized with a certain accuracy, an error message is generated and the user is notified. Individual points can be collected with the Optotrak and stored in a file for use in registration algorithms or other analysis, and an entire set of data points can be collected as well. DLLs may be used for other optical tracking devices, such as the Polaris system from Northern Digital, or other non-optical systems, such as articulated arms.

The registration division 410 consists of all DLLs developed to perform registrations between image space and physical space. A generalized user interface (not shown) is used to select physical and image data models to be passed to the appropriate registration DLL. Within the individual DLLs, specific registration algorithms are used to calculate a mapping between the data sets. The interface of the present invention also allows multiple registrations for a given data set, if desired.

Two point-based registration DLLs map 3-D physical space into 3-D image space using rigid body transformations. One DLL finds a closed-form solution based on unit quaternions to create this transformation matrix. The other DLL uses singular value decomposition (SVD) to find the closed-form solution. In order to determine the transformation matrix, both algorithms require the localization of three or more corresponding non-colinear fiducial points in both 3-D spaces. The SVD algorithm is implemented using the Intel Math Kernel Library, which contains a set of robust math kernel functions that are performance optimized for Pentium processors. Another DLL implements a projective registration algorithm based on the direct linear transformation (DLT). If 6 or more non-coplanar fiducials are accurately localized in the two spaces, a projective registration between 3-D physical space and 2-D endoscopic video space can be created. The Intel library is used to calculate the SVD utilized in the DLT registration. A surface-based registration DLL based on the iterative closest-point algorithm of Besl and McKay is performed using the present invention.

One performance goal of the present invention is to develop accurate registration algorithms. For the rigid body point-based registrations, two measures of error are defined. The residual error determined in mapping the fiducial points from one 3-D space to the other is called fiducial registration error (FRE). If a mapped point not used in the creation of the transformation matrix is compared to its actual position, the difference is referred to as target registration error (TRE). For 600 neurosurgical applications conducted using externally attached fiducial markers for registration purposes, the mean TRE in mapping from physical space to CT image space was 0.67±0.25 mm, with a worse case of 1.15 mm. The accuracy of the DLT registration algorithm used to project 3-D physical space into endoscopic video space has been investigated, and it has been found that registration accuracy improves as more fiducials are used to calculate the transformation matrix. When 11 fiducials are utilized in the computation of the DLT, average TRE is 0.70 mm. Considerable work has been performed in quantifying the accuracy of many other types of registrations as well. All of the registration DLLs developed will return an appropriate quality of fit measure which helps indicate the accuracy of the registration technique(s) utilized in the surgical procedure. If the registration is point-based, a TRE/FRE metric is used for assessing registration quality. If the registration is surface-based, a new metric has been developed which includes holding out certain subsurfaces from inclusion in the registration process. These surfaces are then used as an independent check of registration quality, along with visual assessment.

The display division 415 consists of all the DLLs necessary to display any type of medical image. Two display DLLs have been developed, one type for the display of any tomographic image (MR, CT, PET), and another type for the display of any NTSC video image.

For each child window displaying a tomographic view, a device independent bitmap (DIB) is created. Images are displayed through a bit-block transfer of 8 bit data corresponding to a rectangle of pixels from the specified source device context into a destination device context (i.e., one of the four child windows).

Since most medical images are represented using 4096 individual gray levels (12 bits) and standard video hardware can only display 256 different gray levels (8 bits), some form of compression must be implemented. The compression used by the present invention is piecewise linear and is defined by the window and level parameters. The level parameter determines the uncompressed intensity that is mapped to the middle gray level. The window parameter describes the range of uncompressed intensities surrounding the level value that are mapped to shades of gray. Anything below this window is mapped to black (zero intensity) and anything above the window is mapped as white (full intensity). Tomographic images utilized during surgery are loaded into memory and saved in one of two formats depending on the desired method of display. In one format, the 12 bit/pixel grayscale images are temporarily loaded into memory and compressed to 8 bits/pixel based on the default window and level. The 12 bit images are deleted and the 8 bit images are stored in memory. When the position of the tracked instrument is moved, the appropriate 8 bit image is displayed using a bit-block transfer. Images displayed using this method are updated at greater than 30 Hz when all four windows are displaying tomograms. If the window and level of an image is changed, the entire corresponding volume must be reloaded and each image in the volume is compressed to 8 bits using the new values. The time required to compress the images with the updated window and level varies with the size and quantity of the images. Since a surgeon may want to change the window and level of an image set multiple times during a procedure in order to view different structures more clearly, a second alternative display method may be implemented.

In the alternative display method, the 12 bit volume is loaded just once. Once an appropriate image is selected for viewing, its 12 bit data is compressed to 8 bits based on the given window and level and the resulting DIB is displayed. This "compress on the fly" method allows images to be windowed and leveled without reloading the entire corresponding volume. On our 400 MHz PC, images displayed using this method are updated at 15–20 Hz when all four windows are displaying tomograms. Either method can currently be used for display during surgery. As faster processors are developed, the "compress on the fly" method will update tomograms at an acceptable speed (>30 Hz) to meet performance goals of the present invention and the first method will be eliminated.

Cropped NTSC video images (512×480) are captured with the VigraVision-PCI color frame grabber. This can be used to display an endoscopic or intraoperative ultrasound (IOUS) view. One video image can be updated at 30 Hz in any of the four quadrants. A still video image can be captured and stored in one of several formats, such as a TIFF or a bitmap. When the image is frozen, the position and orientation of the tracked endoscope or IOUS can be saved, and points on the image can be localized and used for projective registration purposes.

Several new display DLLs have been developed for surgical applications. In a graphics DLL, an OpenGL, a 3-D graphics library, is used to render object surfaces created from triangulated tomographic volumes. Tumors or other structures segmented from these volumes can be also rendered and projected onto the object surface to aid in localization. For surgical applications, the rendering view is updated "on the fly" as surgical position is changed. In the rotation DLL, renderings and vascular projection images are created pre-operatively and the desired angular projection is displayed. The position of the probe and trajectory information is projected onto the view according to the reconstruction angle.

Figure 5:
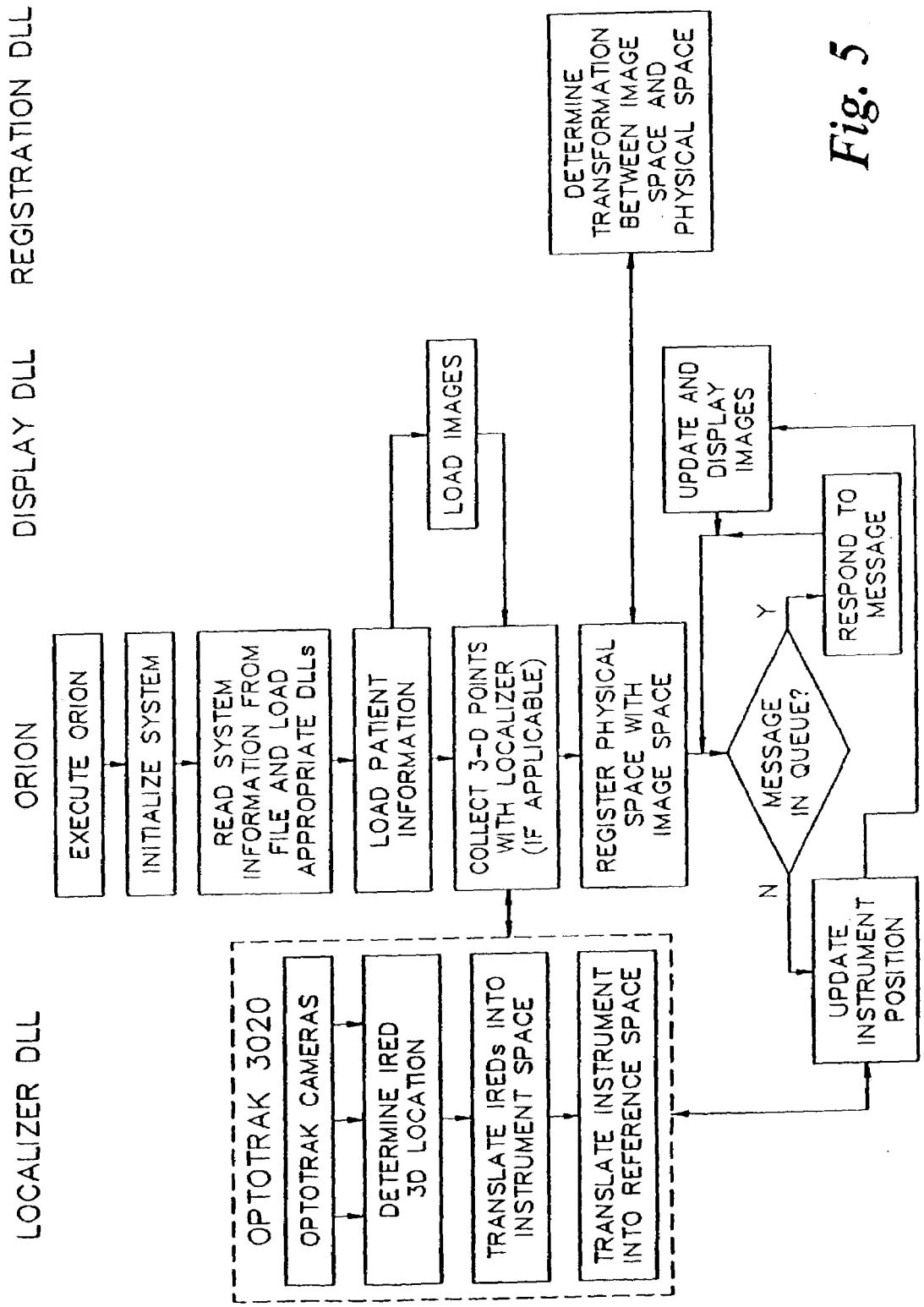
FIG. 5 is a flow chart for software used by the present invention.

FIG. 5 shows a software cycle for image-guided surgery in accordance with the present invention. After execution in Windows NT, the system is initialized and all appropriate DLLs are loaded. A patient information file is then selected from a database. This file contains a list of files indicating image sets that are available for the particular surgical case. Each image set has an associated information file which is included in the patient file. This image information file contains a path to the actual image data, a tag to identify the appropriate DLL for its display, various parameters needed to visualize the data, and all registration types and corresponding image data needed for mapping physical space to image space. Once the image sets are loaded and their child window location is determined, it is usually appropriate to collect some type of physical space data using the localizer DLL. This data may be surface points or fiducial points which can be used in the surface-based or point-based registration algorithms described previously. Physical space and image space data is passed to the appropriate registration DLL and a mapping in the form of a matrix is returned to the present invention. Following registration between physical space and image space, the image sets or other display type is then visualized in some or all of the four child windows. The present invention then enters its message loop and maintains a message queue. The program is now ready to receive any keyboard or mouse input from the user. If there is a message in the queue, the present invention responds to the message and checks for other messages. There is "dead time" in the present invention when the program is idle waiting for messages (e.g., keyboard and mouse inputs). If no messages exist in the queue, the present invention receives matrix information from the localizer DLL concerning the current position of the probe(s) in physical space and passes this and any registration matrices to the appropriate display DLLs. The display DLLs map this physical space position into image space using the appropriate registration result and display the updated images, along with a colored circle to indicate current surgical position.

There are several pushbuttons and mouse commands in the present invention that produce messages. For example, if the user presses the right mouse key in a tomogram display window, the window and level of the image volume can be adjusted. The surgeon can also perform another type of registration, collect some type of physical space data with the tracked instrument, or change the display by pressing one of several pushbuttons on the main window. Each of these tasks are kept behind the simple pushbutton so that during surgery the physician can concentrate on the images displayed. As in the first example, the present invention receives a mouse click over a pushbutton as a message and responds to this request before updating the probe position and the images.

Interactive, image-guided surgery is being utilized in more and more applications, including neurosurgery, spinal surgery, and endonasal surgery. The present invention can be used for general surgical applications, including hepatic surgery.

Surgical treatment of hepatic tumors is performed by removal or ablation of involved segments of the liver. These tumors are localized by preoperative imaging studies, primarily CT imaging, intra-operative ultrasound and palpation. Of these localization techniques only the preoperative tomograms provide high-resolution, 3-D views of the tumor and the surrounding anatomy. However, at present, the tomographic information cannot be actively utilized for surgical guidance in the operating room. Thus, surgeons use other methods for operative tumor localization. It is especially important to accurately localize the tumor during liver ablation procedures, where precise probe placement within the volumetric center of a tumor is critical in the radiofrequency (heat-kill) or cryoablation (freeze-thaw) of the lesion. It is believed that the development of the present invention for hepatic surgery will improve both open and minimally invasive resection and ablation procedures in the liver. Minimally invasive hepatic surgery is currently conducted on a very limited basis. An endoscopic-IIGS system would combine the strengths of real time video imaging and the tomographic guidance from IIGS and make these procedures feasible. Deep-seated tumors which are indicated on CT images will be mapped onto video images of the liver surface using the direct linear transformation (DLT) and then displayed to allow the surgeon more accuracy in performing resections or ablative procedures under endoscopic guidance.

The present invention has been used in the laboratory on phantom livers. These model livers were constructed with rubber silicone, which was poured into a plaster mold along with spherical "tumors" constructed from cork. CT images of the phantom acquired and a surface was created for registration purposes. The surface of the liver is digitized using the tracked probe and the present invention. The registration of the digitized liver surface to the surface of the liver created from the CT scan was calculated using an implementation of the iterative closest point registration algorithm. Experiments using the phantom liver and the described registration technique produced an average registration error of 1.8 mm. This surface registration calculation and the tracked RF probe have been used to localize the centers of "tumors" within the phantom on the CT images, and it was possible to place the tip of the instrument to within 1.2–6.0 mm of tumor centroids. Errors in this range can be achieved using the surface of the liver intraoperatively.

Experiments have been also conducted to develop a surgical protocol for using the present invention for open hepatic resection in patients with liver tumors, and tracked points on the liver to determine respiratory associated hepatic movement. An ablative instrument was placed on three anatomical points on the liver. Approximately 950 localization points (x, y, z) are continuously collected using the present invention. Each patient (n=2) had >2800 localization points collected during continuous respiratory cycles with standard continuous mandatory ventilator cycling. The change in position of the tracked points with respiration was calculated relative to the resting base position of the liver. Average motion with respiration for all anatomical points was 10.3±2.5 mm.

Interactive, image-guided surgery has improved the quality and feasibility of many surgical procedures, including neurosurgery and ENT surgery. It is crucial that these systems provide measures of system performance in a manner which parallels the surgical process. The systems must provide fast and accurate registration processes to map physical space into image space, and must also include instruments which precisely indicate current surgical position. In addition, images must be displayed and updated in real time to allow ease in tracking structures across slices or surface renderings.

A Windows-based image-guided surgical system has been developed on a low cost personal computer with an active optical tracking system. The present invention was developed in Visual C++ with the Win32 API for windows management. Since the present invention was developed using a module library for each of the different components, code migration and maintenance is simplified. At any given time, a subtask contained within a particular DLL used in the system can be "checked out" of a Visual C++ SourceSafe database that stores the most recently edited master copy.

The present invention is capable of applications beyond neurosurgery, including open and minimally invasive hepatic procedures. Target errors on the order of 2 mm for the phantom registration studies were higher than those seen in clinical neurosurgical cases. This number is acceptable since the liver is much more homogeneous than the brain and higher accuracy is not as critical an issue.

In one preferred embodiment of the present invention, laser range scanners are used to provide rapid and accurate non-contact methods for acquiring three-dimensional surface data, offering many advantages over other techniques currently available during surgery. The range scanner may be incorporated into an image-guided surgery system to augment registration and deformation compensation. A rigid body, embedded with infrared diodes, is attached to the scanner for tracking in physical space with an optical localization system. The relationship between the scanner's coordinate system and the tracked rigid body is determined using a calibration phantom. Tracking of the scanner using the calibration phantom results in an error of 1.4±0.8 mm (n=234). Once tracked, data acquired intraoperatively from the range scanner data is registered with preoperative tomographic volumes using an Iterative Closest Point (ICP) algorithm. In cases where tissue deformation is significant, rigid registrations can lead to inaccuracy during surgical navigation. Methods of non-rigid compensation may require the use of a linearly elastic finite element model. Differences between intraoperative and preoperative surfaces after rigid registration are used to formulate boundary conditions, and the resulting displacement field deforms the preoperative image volume. A phantom consisting of fiducial points and a silicone liver model may be built to test the model, where range scan and CT data captured both before and after deforming the organ are compared. The rigid registration accounts for most of the error from deformation, although there may be a noticeable improvement by implementing the finite element model. To improve accuracy, more elaborate surface registration and deformation compensation strategies may be used. The range scanner is an innovative, uncumbersome, and relatively inexpensive method of collecting intraoperative data.

An image-guided surgery system for use with liver procedures may include a means of acquiring three-dimensional surface data through the use of a laser range scanner which outputs a dense set of three-dimensional point data that is used to register with preoperative images by means of a rigid surface-based registration algorithm. Laser range scanning has been used for registration in neurosurgical procedures using mutual information techniques which align the cortical vasculature, as well as surface based techniques used to match cortical surface topology in phantoms and features on the human face. Range scanning also provides a rapid method of acquisition, so that a large amount of data can be acquired in one short period of held respiration. Initial laser range scans performed during surgery have shown a good fit with preoperative CT volumes, although there is some deformation present. The scanner must be tracked in physical space so it can be linked with other localization systems. Correction mechanisms for tissue deformation are implemented, based on the resulting range scan data. These corrections can be rooted in biomechanics through implementation of a finite element modeling technique, or they could be more interpolative in nature by introducing splines.

Figure 6:
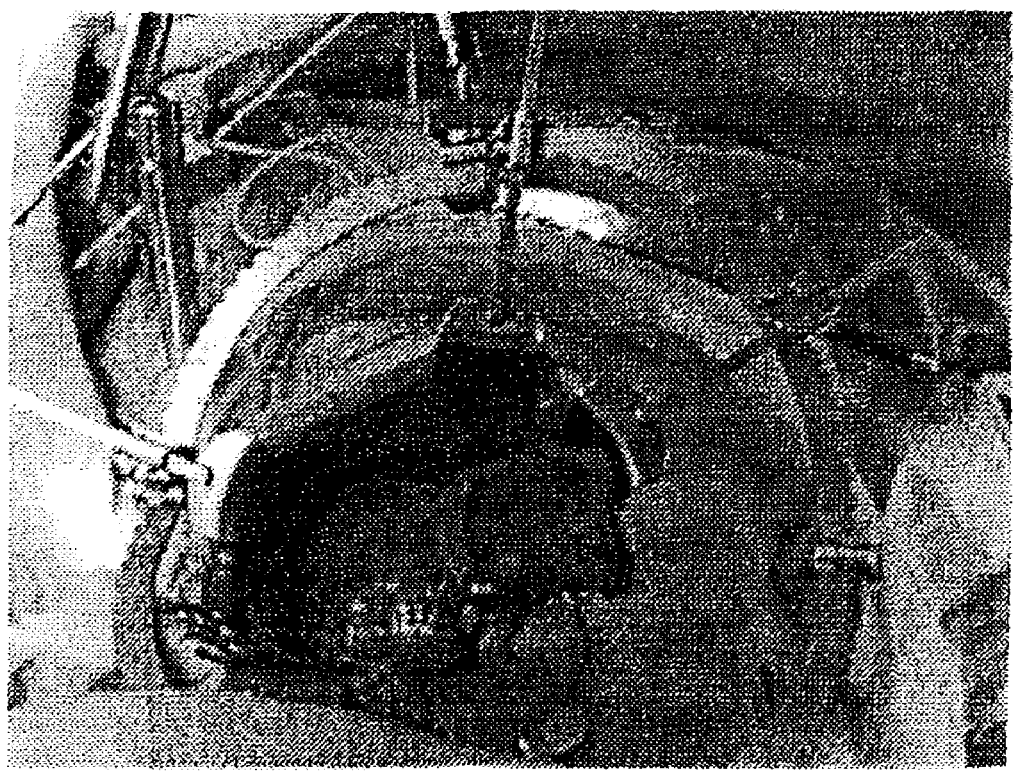
FIG. 6 shows surgically exposed tissue of a living patient.
Figure 7A:
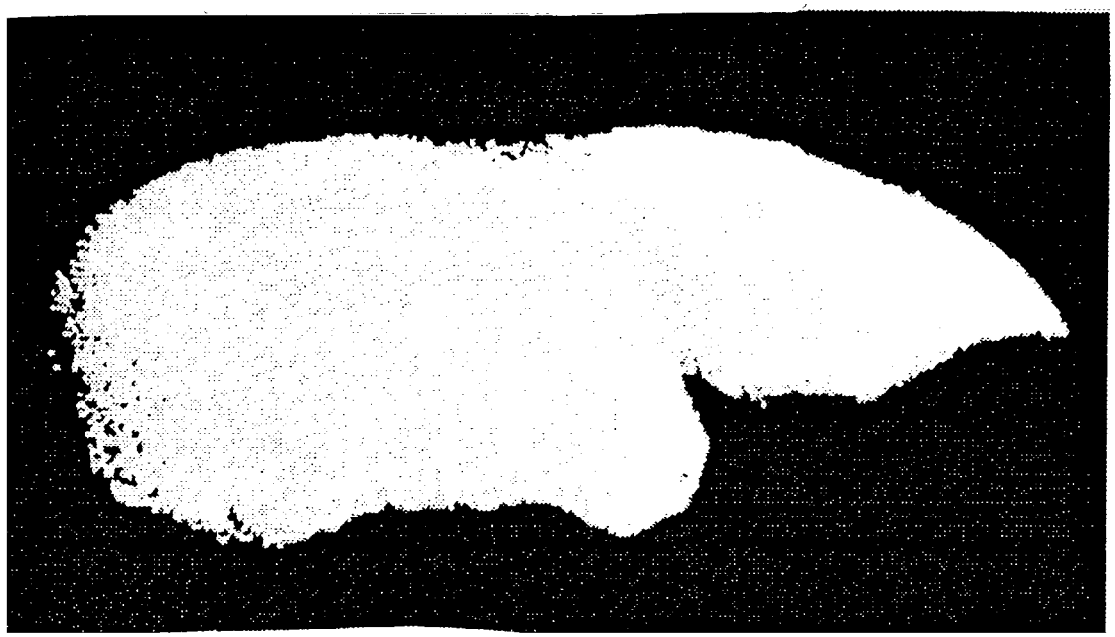
FIG. 7A shows a laser range scan of the exposed tissue of FIG. 6 whereby a video image is acquired of the scene by a laser scanner.
Figure 7B:
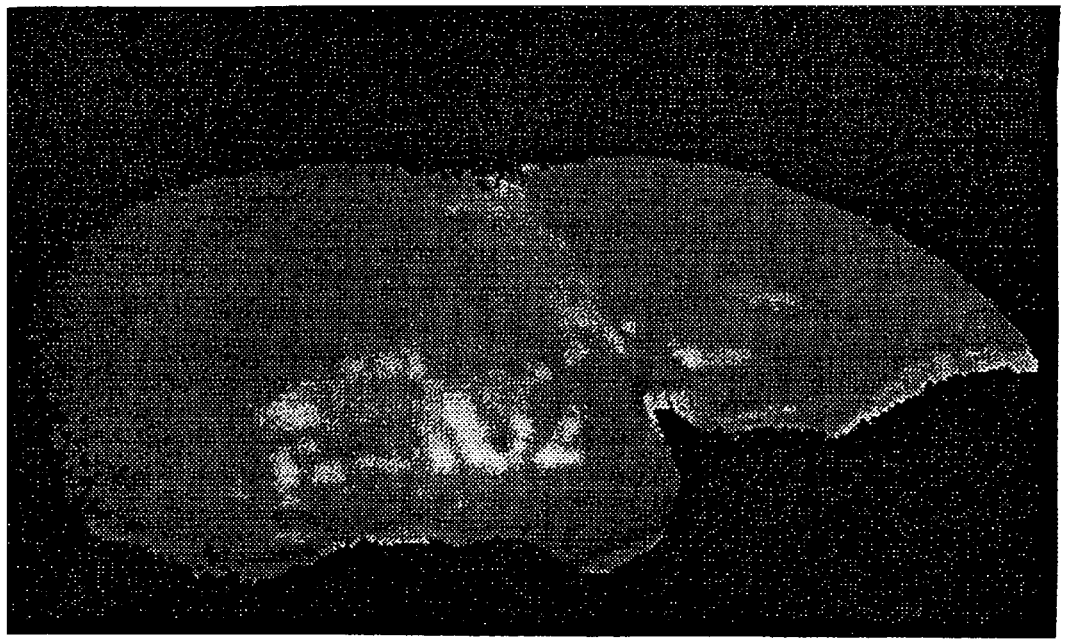
FIG. 7B shows the laser range scan of FIG. 7A texture mapped onto the range data, so that each point contains color information.

To acquire dense surface information of the liver during surgery, a laser range scanner working on the optical principle of triangulation is used. Laser light is emitted from the range scanner and illuminates the surface of surgically exposed tissue of a living patient (see FIG. 6). The light reflected from the surface is received by a charged-couple device (CCD) array within the range scanner, which has a known geometrical relationship with respect to the source. The depth is calculated based on this relationship and the calculated center of the received light pattern. The laser range scanner used in our surgical navigation system spreads the point source out into a vertical stripe to simultaneously calculate numerous range scan sample points. The laser range scanner is capable of scanning 500 lines per scene, and as many as 512 samples per line. In addition, when scanning at 256 samples per line, a video image is taken directly after range scan acquisition (see FIG. 7A), and this image is texture mapped onto each point by a predetermined calibration function, so that color information can be acquired in every point (see FIG. 7B). While the color information is not used for this specific registration algorithm, it proves to be very useful in the identification of the liver within an intraoperative scene. Total acquisition time takes 5–20 seconds.

Figure 8:
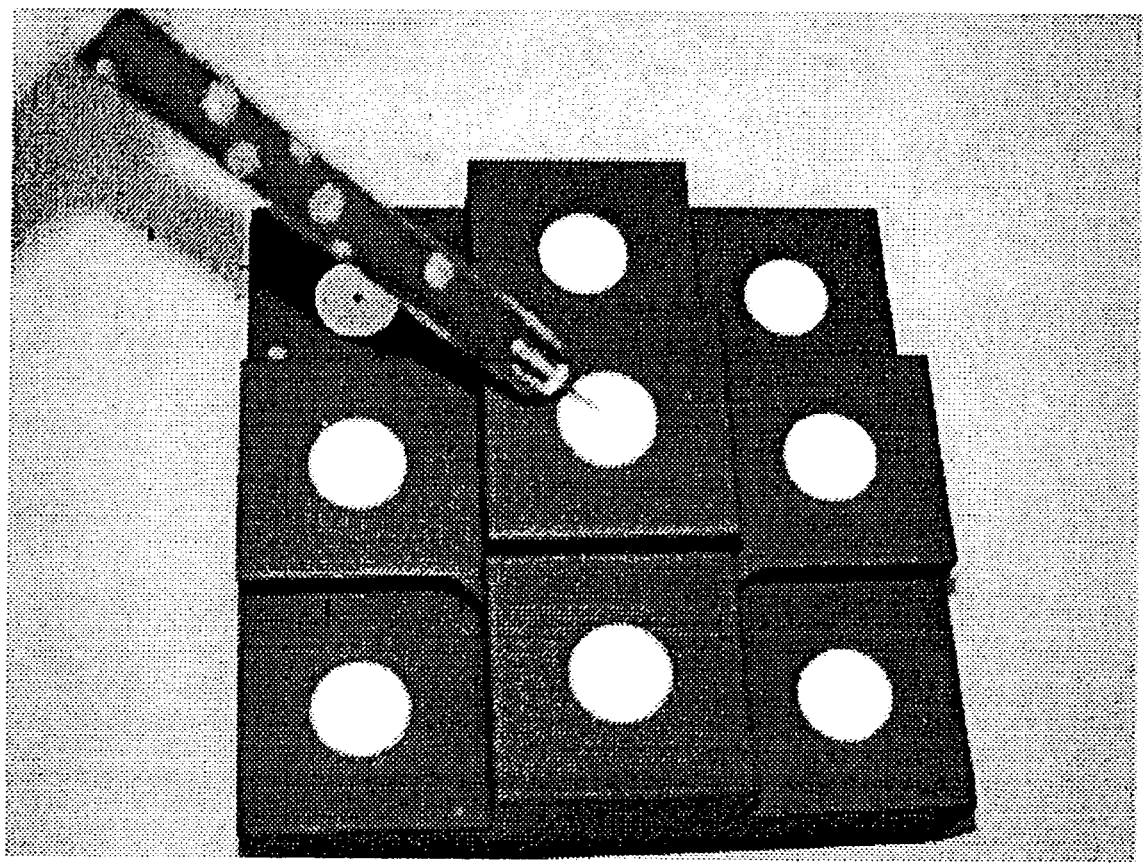
FIG. 8 shows an exemplary calibration phantom used in conjunction with the laser scanner.

In order for range scan data to be used in the same coordinate system as tracked surgical instruments, it must also be tracked by an optical localization device. A rigid body is affixed to the range scanner, and this rigid body contains Infrared Emitting Diodes (IREDs), which are recognized by the localizer. The relationship between the coordinate systems described by this rigid body and the range scanner is determined through a calibration procedure using a phantom. FIG. 8 shows an example of a calibration phantom (dimensions: 15.0 cm (L)×15.0 cm (W)×6.0 cm (H)), consists of nine separate platforms of varying height. In each platform, a white cylindrical disc of radius 9.5 mm is inserted flush to the platform. The rest of each platform is painted with a non-reflective black paint so that most of the range scan data of the phantom not representing the disk is eliminated, thus making identification of each disk easier. From the range scan of the phantom, all nine discs are identified and their centroids are calculated. A hemispherical divot of 3.0 mm diameter is precisely machined in the center of each disk, so that when the 3.0 mm ball tip of a tracked surgical probe is placed into the divot, the centroid of the ball tip corresponds to the centroid of the disk. The resulting two sets of data are used to determine a registration between range scan space and physical space. With this registration, and the position and orientation of the rigid body affixed to the range scanner, a calibration transformation is established. This transformation is between the range scanner and the affixed rigid body, and it will remain fixed throughout the procedure.

Figure 9:
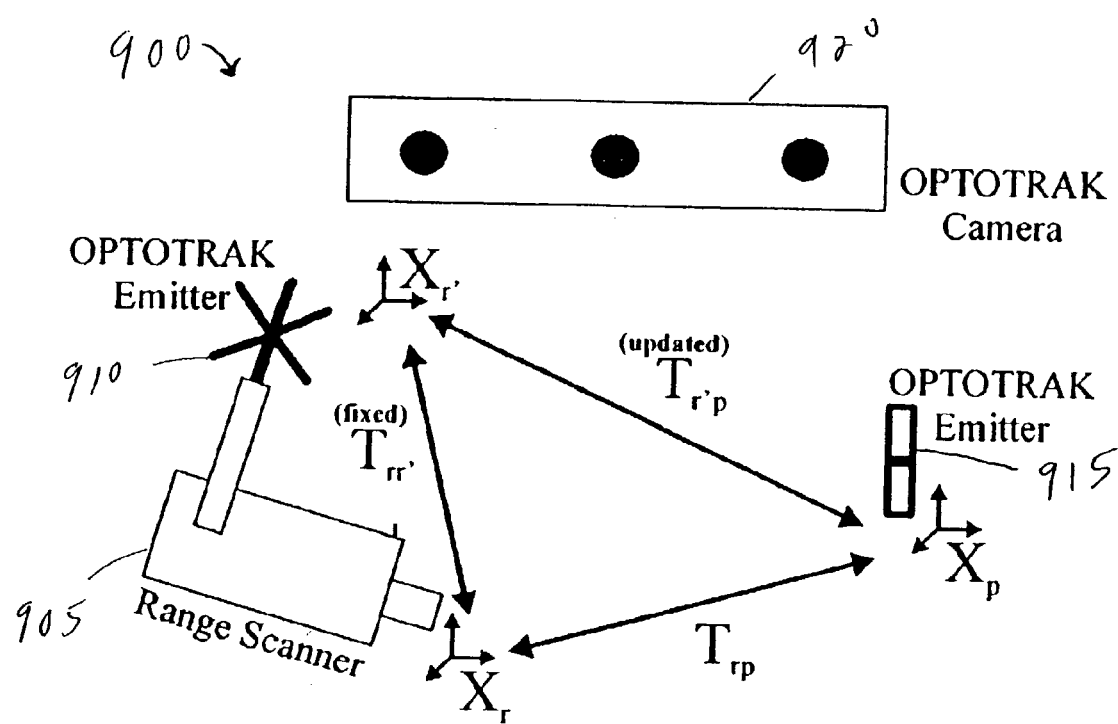
FIG. 9 shows a calibration process used in conjunction with the laser scanner.

FIG. 9 shows a calibration process to determine the fixed transformation ($T_{rr'}$) between a range scanner 905 ($X_r$) and an OPTOTRAK emitter 910 ($X_{r'}$) attached to the range scanner 905 ($X_r$). $T_{rr'}$ is determined from the transformation between the range scanner 905 and physical space ($T_{rp}$), and from an OPTOTRAK emitter 915 ($T_p$), which can be updated.). An OPTOTRAK camera 920 (i.e., optical tracking sensor) contains three cylindrical lenses which receive signals from the OPTOTRAK emitters 910, 915 to find each emitter relative to the position of the OPTOTRAK camera 920.

Light from sequentially strobed infrared light-emitting diodes (IREDs). Triangulation is used to find each IRED relative to the position of the optical tracking sensor 325.

Two sets of experiments may be performed regarding tracking of the range scanner 905. The first set of experiments involved registration experiments between the OPTOTRAK emitter 915 and the range scanner 905. For every nine points of data generated in a trial, all 126 combinations of 5 targets and 4 fiducials are determined. A point-based registration is performed for each of these sets, and Fiducial and Target Registration Error are calculated. The second set of experiments that is performed involves using the phantom for tracking. Data is acquired during a calibration trial from both physical space and range scanner space, and a calibration transformation is determined. Subsequent trials of data are then taken for both spaces. In between trials, the range scanner is brought out of and back into the field of view to simulate the process that occurs in surgery. Rather than registering the data, the calibration trial is used to determine the position of range scan points in physical space. These transformed points are compared to physical data acquired by the range scan data. Every trial acquired is used one time as the calibration trial.

Rigid registration between image and physical data is achieved using the Iterative Closest Point algorithm, modified to use k-d trees in order to decrease search time during closest point calculations. Abdominal CT volumes are acquired, and the liver is segmented from this images using manual delineation or a semi-automatic method based on the level-set method. The contours are used in registrations with data from the range scanner and tracked probes. An initial alignment is required with the ICP algorithm in order to avoid local minimum, which is achieved using anatomical landmarks on the liver surface. To test the sensitivity of the surface based registration, a series of registrations are performed while perturbing the initial alignment by one of the degrees of freedom. These registrations are performed on one data set in which the inferior ridge was completely exposed, and another which only part of the inferior ridge was available.

While the Fiducial Registration Error is approximately 4–5 mm for landmark registration in phantoms, it is very difficult to localize landmarks during surgery. In clinical cases, Fiducial Registration Error based on landmarks can be as large as 25 mm. To avoid relying on fiducial localization in the operating room, an initial alignment based on the Hotelling transform has been implemented. The Hotelling transform aligns the data sets according to their principal axes, which are calculated from the eigenvectors of the segmented point set's covariance matrix. Since only a fraction of the liver is exposed to the range scanner, a preprocessing step of eliminating non-exposed surface data from the image contours is necessary. In virtually all open abdominal procedures, a majority of the anterior surface of the liver as well as the inferior ridge at Sections III, IV, and V of the Couinaud segments is available for data acquisition. A reference direction is assigned in order to avoid right-handed coordinate systems in which two axes are inverted. This reference direction is assigned at the time of surface acquisition to determine the direction of two of the principal axes. A convention was decided that the reference direction would point caudally towards the left lobe, and that this would represent the positive x and y principal axes.

Figure 10A:
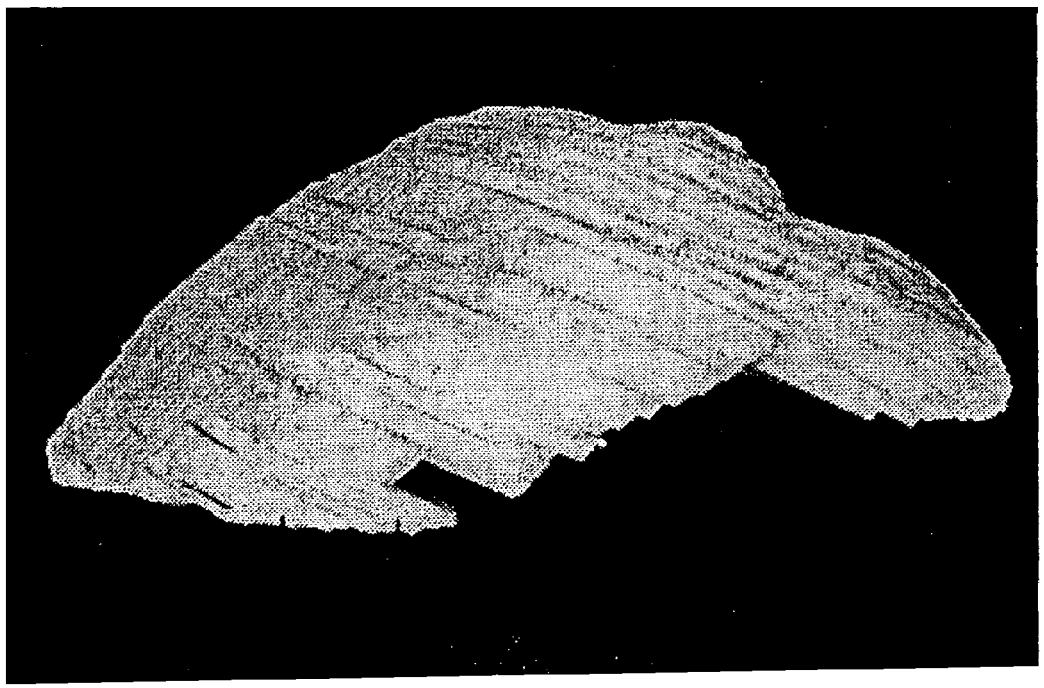
FIGS. 10A and 10B show a registration between image data and range scan data.
Figure 10B:
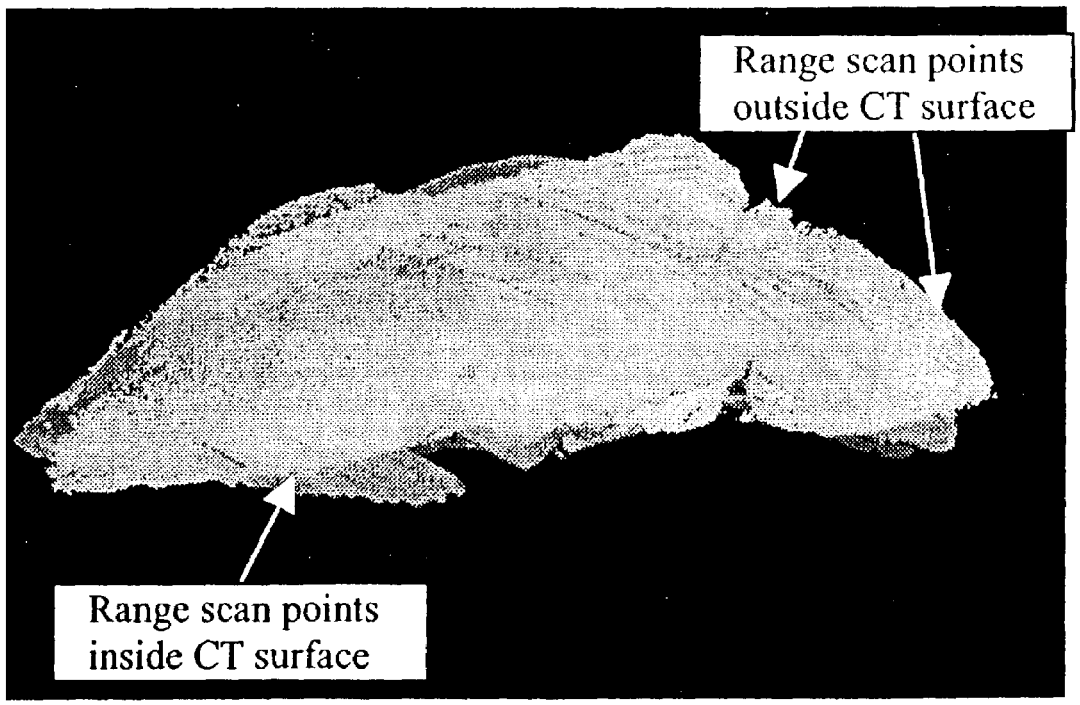

FIGS. 10A and 10B show a registration between image data and range scan data from a clinical case. FIG. 10A shows a triangulated surface from segmented CT data. FIG. 10B shows registered range scan point data overlaid on the surface. The white arrows point to areas where deformation is exhibited.

From visual inspection, there is a noticeable shape change between the preoperative imaging studies and intraoperative presentation. Compensation for this deformation after rigid registration is being considered. In preliminary studies, a three-dimensional linearly elastic finite element model has been chosen for the compensation. The data is first registered using a rigid surface registration, and then modeling is performed using a finite element mesh generated from the preoperative image data. The resulting closest point correspondences at the end of the registration will be used to construct boundary conditions in terms of normal displacements.

Deformation studies are performed using a liver phantom. The phantom consists of three components: a poly (dimethyl) siloxane (rubber silicone) model of the liver, seven white Teflon spheres machined to 12.70 mm with a 25 µm tolerance, and a black Plexiglass base to eliminate unwanted range scan data. Fiducial data was acquired by fitting the range scan representation of each sphere's surface using a least-squares geometric method. All of the components are easily differentiated in both range scan and CT images. The phantom was imaged with CT, and a range scan was acquired immediately after, while keeping the phantom on the imaging gantry. This set of data served as a preoperative baseline. Then, a plastic cylindrical object of 3.7 cm height was placed underneath the phantom for the purpose of deformation. Another CT volume and range scan was acquired while the organ was deformed. Mock tumors made of Styrofoam spheres are placed in the organ while constructing the mold, and the centroid of these tumors in both preoperative non-deformed and intraoperative deformed volumes are identified. Distances between corresponding tumors are calculated after a point-based registration based on the Teflon spheres to determine the initial displacement, after a rigid surface registration using ICP, and after correction using the finite element model.

In order to handle the requirements of surface acquisition and deformation compensation during image-guided liver surgery, two new components have been developed for ORION. The first component was an I/O DLL designed to communicate with the laser range scanner for data acquisition. The range scanner is connected to the surgery computer through a Universal Serial Bus (USB) connection, and the software interface developed by the manufacturer is written as an ActiveX control. The DLL was implemented in C++ using MFC. Once the data is acquired, it is displayed in one of the four display windows, where it could be rotated, zoomed, edited, and saved to disk.

To handle compensation strategies, a new correction class of DLL was developed. This correction DLL handles non-linear manipulation of images, such as finite element modeling and non-rigid registration. A description file, detailing the parameters and data to be used in the correction process is passed into ORION, and on to the correction DLL. For the finite element model, this file will hold the locations of the node, element, and boundary descriptions of the mesh to be used. The DLL will generate and warp the preoperative image, such that a new image is formed which has the same rigid registration as the preoperative image. Corrections will be performed as needed during surgery, using intraoperative data from ultrasound and range scanning.

During patient preparation, the OPTOTRAK camera, range scanner, and computer are brought into the operating room. Surface points are acquired using a tracked surgical probe in contact with the liver surface. The probe acquires new points at a rate of 40 Hz, or a total of 2400 points per minute. During acquisition, the patient undergoes a brief anesthetically induced apneic period. During this apneic period, 100% Oxygen is placed into the airways so that the blood stream receives enough O2 through diffusion. However, there is a concern about CO2 buildup during the apneic periods, so pH is carefully monitored by the anesthesiologist. Range scan surfaces of the operative scene are acquired, as are regions of the liver by placing a tracked probe directly on the surface. Most of the tracked probe data will be for specific areas of interest, such as the inferior ridge or the falciform groove.

For range scanning in the OR, the tracking calibration procedure is performed before the patient is placed in the operating room. The range scanner is mounted on a surgical arm, so that it can easily be moved out of the surgeon's way. The scanner is brought near to the surgical field over the lower abdomen, and acquires a scan 2–3 feet away from the exposed liver. Preparation for a scan takes about 60 seconds, in which holding the patient's respiration is not necessary. Then, there is an apneic period during a 20 second range scan, and afterwards, surgery resumes while image processing and registration take place.

A total of twelve registration trials have been performed using the calibration phantom. From the nine points available for each trial, there are a total of 126 unique combinations of 5 fiducials and 4 targets, which resulted in a total of 7,560 individual fiducial error measurements and 6048 individual target error measurements. The mean fiducial registration error was 1.02±0.56 mm, with a maximum error 3.79 mm, and the mean target registration error was 1.39±0.71 mm, with a maximum of 4.81 mm.

Tracking experiments are performed in two sets of trials, with five trials in one set and three trials in the other. Each trial served one time as the calibration trial, and using the calibration matrix from this trial, range scan points are transformed into physical space and compared to the actual OPTOTRAK configurations. This resulted in 36 samples for each trial in the first set (9 data points each for the four non-calibration trials) and 18 points for each trial in the second set. The overall tracking error with the phantom was 1.43±0.55 mm over 243 samples.

FIG. 11 shows tracking results from the calibration procedure. Each trial served once as the calibration trial, and the calibration matrix of the trial was used on all of the other related sets of data.

Figure 12A:
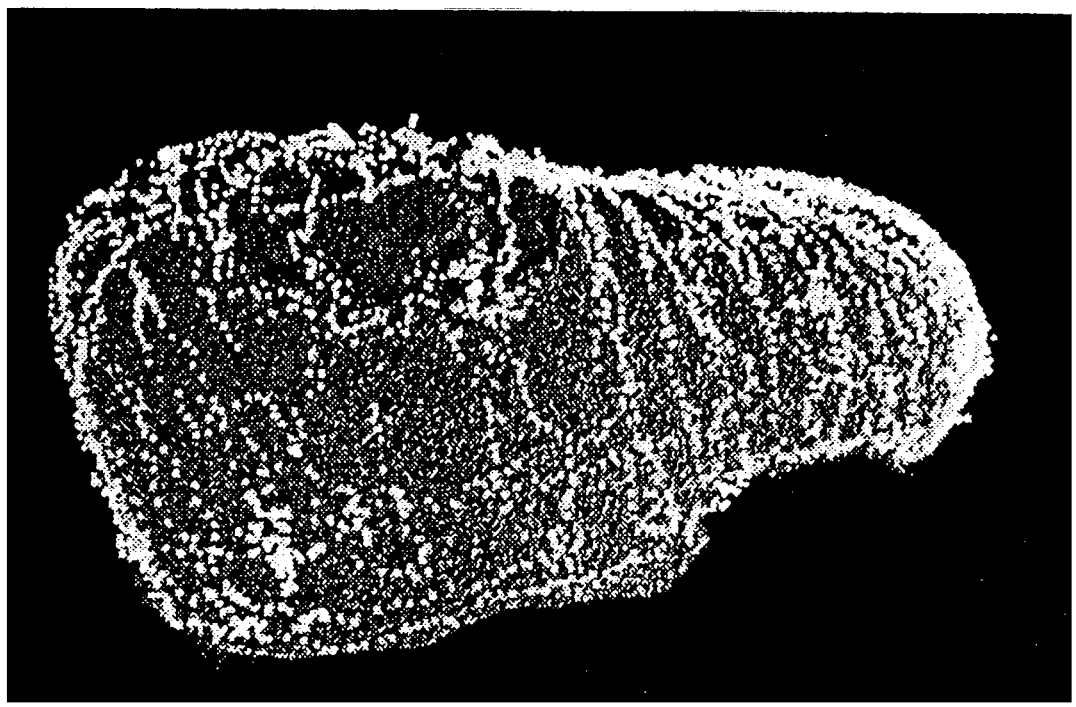
FIGS. 12A and 12B show experimental results from a range scanner studies using a liver phantom.
Figure 12B:
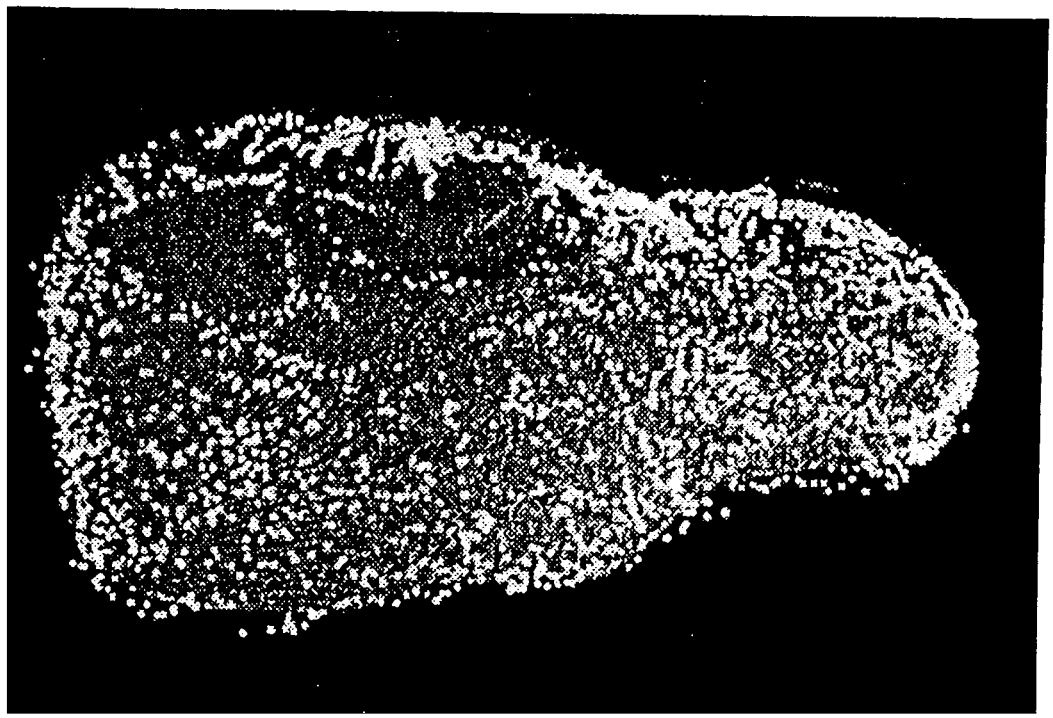

FIGS. 12A and 12B show the application of the calibration procedure to the liver phantom including the overlay of range scan data on top of physical space data of the liver phantom acquired with a tracked probe. No registration is performed between these two surfaces, as they are aligned only by use of the calibration matrix and the position of the rigid body emitter affixed to the range scanner. The mean closest point distance for the overlapping regions of these surfaces is 1.5±1.0 mm (n=2372 points) as shown in FIG. 12A and 2.2±1.6 (n=2268 points) as shown in FIG. 12B.

FIG. 13 shows tracking results from the calibration phantom. Each trial served once as the calibration trial, and the calibration matrix used for the trial was used on all the other related sets of data. A successful range scan is defined based on visual alignment and mean closest point residual. Typically there is a difference on the order of 4–5 mm mean closest point residual between a "success" and a "failure". Of the 396 studies performed on data with an incomplete ridge, 30 failed, most occurring due to a rotation in the X and Z-axes. However, with a better definition of the ridge, only one trial failed out of 455. All the successful registrations are used to transform the physical data into image space, and a mean transformed position was calculated for each point in the physical data. A deviation from the mean points was calculated using all the successful registrations in order to determine the precision of the final results from each ICP registration.

An additional sensitivity study was also performed to determine the robustness of the initial alignment by Hotelling transform. 100 trials were performed in which the initial transformation, either landmark-based or Hotelling-based, was perturbed randomly in all six degrees of freedom. The limit of perturbation was (−20 mm, +20 mm) for all translations and (−10°, 10°) for all rotations. In both cases, all 100 trials were successes, and the average distance from the mean registered position was 1.1±0.2 mm for the Hotelling transform and 0.9±0.1 mm for the landmark based transform.

Figure 14A:
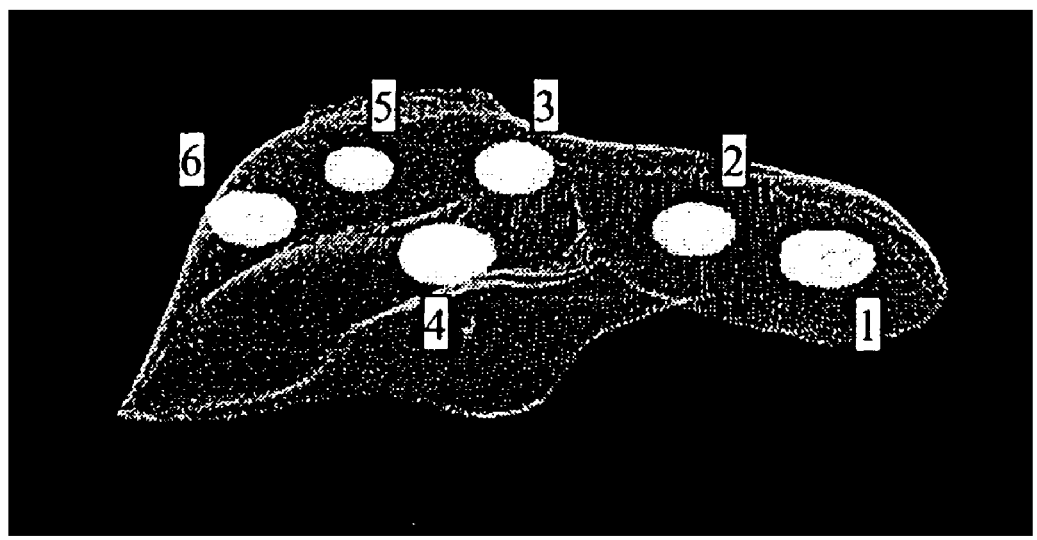
FIG. 14A shows a non-deformed liver surface from a segmented CD surface.
Figure 14B:
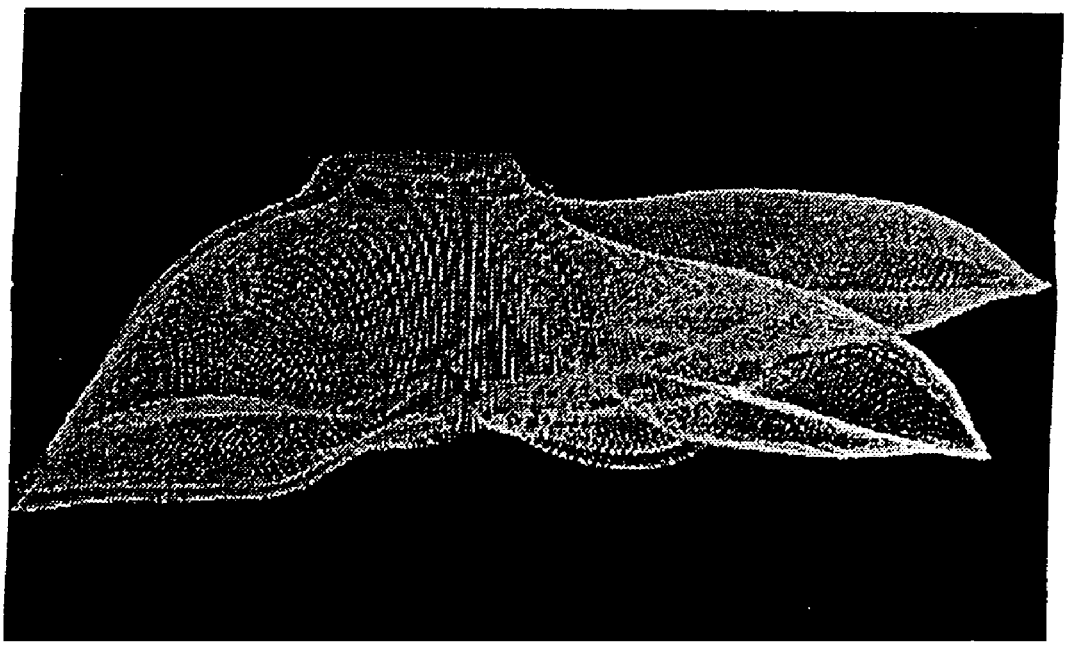
FIG. 14B shows CT surfaces from non-deformed and deformed image volumes.

The position of the six mock tumors in relation to the non-deformed surface is shown in FIG. 14A, and the difference of the CT surface before and after deformation is shown in FIG. 14B. FIG. 14A shows a non-deformed liver surface from segmented CD surface. The white spheres indicate the location of the mock tumors, and the numbers coincide with those in FIG. 15. FIG. 14B show CT surfaces from non-deformed and deformed image volumes.

FIG. 15 shows results from the deformation studies. The first percentage reports the change between the initial error and the rigid error. The second percentage is the percent change between modeling and surface registration in terms of the initial error, while the last column indicates the amount of improvement with respect to the rigid error. The overall error between tumors decreased nearly 70% due to the rigid registration, although there was an increase in error for two of the tumors. Deformation compensation accounted for another 6% decrease in overall error, and no significant increases in error.

Figure 16:
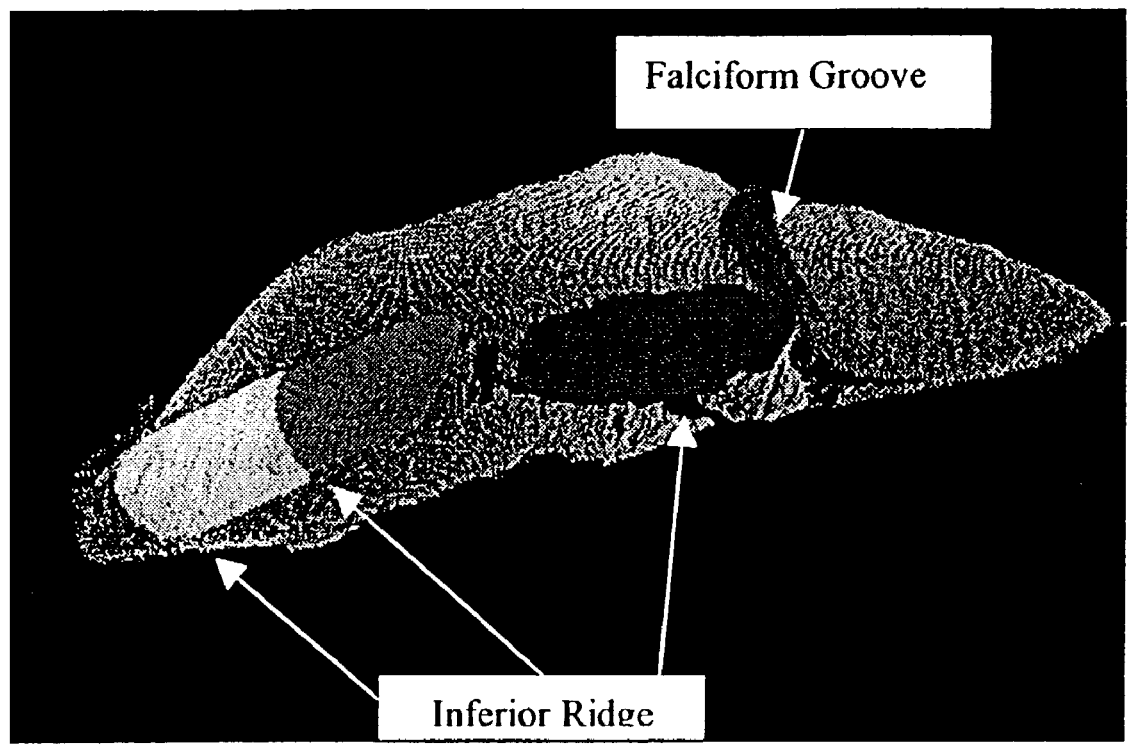
FIG. 16 shows the locations of the inferior ridge and falciform groove of a liver phantom.

One of the primary challenges to this research is the validation of registration accuracy. Since there is no landmark data available for fiducials, there are also no landmarks that can serve as targets in order to verify the registration. However, there are regions on the liver that contain geometrically rich features and could be localized with enough confidence to serve in a manner similar to a point-based target. The two most likely candidates are the inferior ridge of the liver and the groove underneath the falciform ligament, which are highlighted in FIG. 16. There have been many different uses of surface geometry for registration, including surface normals, principal curvatures, extremal points, crest and ridge lines. Ridgeline descriptions have been used in a manner similar to fiducials for registration of a liver phantom. The inferior ridgeline may play a stabilizing role in the registration. This ridgeline provides more uniqueness to the surface being registered and eliminates some local minima. However, not all of the ridgeline may be needed for use in the registration. Initial studies have focused on using only part of the ridge data for the registration, allowing the rest of the ridge to be used as target data. Rather than calculating closest point distance for the target metric, the surface is tessellated, and normals are projected from each range scan point onto the image surface. While this still does not provide a one to one correspondence, it does allow the surface invariant features of the liver surface to play a greater role in the error calculation. Automatic detection of regions with unique geometric signatures and more advanced error metrics are being pursued.

Once sufficient targeting on the surface has been achieved, more invasive targeting methods will be explored.

Finite element modeling has been widely examined in with respect to the problem of brain shift. It provides an inexpensive way of updating during surgery compared to intraoperative tomographic imaging. In terms of the deformations experienced in brain shift, the example presented with the phantom herein may seem a bit extreme. However, the type of deformation that is experienced in open abdominal surgery is much more of a gross shape change than a subtle deformation. The rigid ICP-based registration reduces a considerable amount of error at areas of large deformation by spreading this error across the entire surface. Although this strategy is shown to be beneficial in the results presented here, the method does not provide information that characterizes the extent of deformation during intraoperative presentation of the liver. However, observations during surgery have indicated that certain regions of the liver apparently undergo less shape change. If these areas could be identified systematically a priori, modifications to the ICP algorithm could be employed (e.g. added regional weighting) to aid in differentiating deformation from rigid body motion. Other methods of deformation, such as spline-based interpolation will be compared with the finite element to determine which method is better suited to handle the non-rigid component of the shape change.

The deformation did show improvement in locating tumor centroids. However, the improvement could be larger in clinical cases, since the deformation experiment performed with the phantom does not completely represent the data acquired in surgery. First, there is significantly less coverage of the liver surface by the range scanner in the operating room. While about 52% of the entire surface area is acquired on the phantom, only 25% is available during surgery. In addition, the liver phantom has more geometrically unique regions available for the range scanner than is observed during surgery. Finally, there will be more than one source of deformation in the operating room, removing some of the rigid component of this deformation. These three factors result in a rigid registration that can provide better compensation for the deformation, thus leaving little room for improvement by the finite element model.

The components and protocols for an image-guided liver surgery system includes integrated interfaces for rapid surface acquisition with a range scanner and non-rigid correction with a finite element modeling. Initial studies with phantom show that tracking is highly accurate, and that deformation correction can improve the error of subsurface targets. However, for very large deformations, a rigid component that can be compensated through registration is more dominant. Various deformation strategies will need to be compared to determine which method will be optimal. Sensitivity studies on clinical data show that surface registrations are highly robust to changes in initial alignment if a well-defined ridge is present in both sets of data.

Image-Guided Surgery requires four things:

(1) a set of images from the patient;

(2) a three (or six) dimensional tracking system;

(3) a method of registration for mapping physical space locations into image-space locations; and (4) the ability to display position and orientation of the tracked object to the surgeon.

While there was considerable early work on articulated arms and sonic triangulation systems, optical triangulation systems have emerged as the dominant methodology of three-dimensional localization for surgery.

However, optical techniques have a few drawbacks, the chief of which being a requirement of the maintenance of a line of sight between the optical detector and the tracked object. This means that optically tracked objects cannot disappear into the patient and still be localized. Thus, there has been considerable rise in interest in magnetic tracking systems which can be placed inside a living patient and still be tracked.

Magnetic trackers work on the concept that as one moves away from a magnetic field it falls off quite rapidly. The sharpness of that drop means that the distance can be calculated with a small error. The problem is that the orientation of the detectors to the field can also affect its size, therefore you cannot distinguish single signal loss due to orientation from distance. Thus, these systems must make multiple measurements to sort out the issue by either multiple sources or multiple detectors bound together in a rigid configuration, or some combination of both.

For multiple sources, a first source is turned on to make a measurement. The first source is then turned off and a second source is turned on to make a measurement. There are two fundamental problems with this approach. First, it requires that the sensor be motionless while you turn on and off the sources. Second, magnetic fields cause transient changes in induced current in nearby metal. This can "warp" the field making measurement troublesome until those transients die out. However, such systems can have a substantial range (i.e., meters).

For multiple sources at different frequencies, the sources can stay on all of the time. The effect can be sorted on a one-to-one basis by filtering only one frequency. Thus, there is less distortion. However, the range is limited.

The shapes of magnet fields do not necessarily have to be spherical. Instead, they can be made to be flat oblong tear-drop shapes. Thus, the object is sorted by the correction of the estimated position of the object with the field shape. When the sources stay on all of the time, the range is reduced even more (i.e., 10's of cm's). Using a phased array, a transmitter is tracked and several receive antennas are arranged in a known configuration. By measuring the signal at numerous locations, the position and orientation can be tracked.

When using magnetic tracking, one or more magnetic fields of known shape and frequency are established. The location of an instrument object is located by measuring the detected strength of each established field and processing that data.

The present invention may be implemented with any combination of hardware and software. If implemented as a computer-implemented apparatus, the present invention is implemented using means for performing all of the steps and functions described above.

The present invention can be included in an article of manufacture (e.g., one or more computer program products) having, for instance, computer useable media. The media has embodied therein, for instance, computer readable program code means for providing and facilitating the mechanisms of the present invention. The article of manufacture can be included as part of a computer system or sold separately.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method of collecting and processing physical space data for use while performing image-guided surgery, the method comprising:
   (a) surgically exposing tissue within a living patient;
   (b) collecting physical space data by (i) illuminating the surface of the exposed tissue within the living patient with laser light, (ii) receiving light reflected from the illuminated surface of the exposed tissue within the living patient, and (iii) performing an analysis on the reflected light, the physical space data providing three-dimensional (3-D) coordinates for each of a plurality of scanned surface points;
   (c) based on the physical space data collected in step (b), determining registrations used to indicate surgical position in both image space and physical space;
   (d) using the registrations determined in step (c) to map into image space,
      (i) image data describing the physical space of an ablative instrument used to perform the image-guided surgery,
      (ii) an ablation zone of the instrument,
      (iii) the tissue, and
      (iv) a particular portion of the tissue to be resected or ablated;
   (e) taking a video image after collecting the physical space data; and
   (f) texture mapping the video image onto each registration by a dynamic calibration function.

2. The method of claim 1 further comprising:
   (f) prior to performing the image-guided surgery, scanning tissue of the patient to acquire, store and process a 3-D reference;
   (g) creating a triangularized mesh based on the scanned tissue of step (e); and
   (h) determining the volumetric center of a particular portion of the tissue to be resected or ablated during the surgery, wherein an algorithm using the triangularized mesh and the physical space data collected in step (b) is implemented to determine the registrations in step (c).

3. The method of claim 2 wherein the algorithm is an iterative closest point (ICP) registration algorithm.

4. The method of claim 1 wherein the tissue is the patient's liver and the particular portion of tissue to be resected or ablated is a hepatic metastatic tumor.

5. The method of claim 1, wherein step (b) is performed using a laser range scanner that is freely movable and not rigidly fixed during scanning.

6. The method of claim 5, further comprising:
   (g) tracking the portable laser range scanner.

7. Apparatus for collecting and processing physical space data for use while performing image-guided surgery, the apparatus comprising:
   (a) a laser scanner for collecting physical space data by (i) illuminating the surface of surgically exposed tissue within a living patient with laser light, (ii) receiving light reflected from the illuminated surface of the exposed tissue within the living patient, and (iii) performing an analysis on the reflected light, the physical space data providing three-dimensional (3-D) coordinates for each of a plurality of scanned surface points;
   (b) an ablative instrument for resecting or ablating a particular portion of the exposed tissue;
   (c) an image data processor comprising a computer-readable medium holding computer-executable instructions for:
      (i) based on the physical space data collected by the laser scanner, determining registrations used to indicate surgical position in both image space and physical space; and
      (ii) using the registrations to map into image space,
         a) data describing the physical space of the ablative instrument,
         b) an ablation zone of the instrument,
         c) the tissue, and
         d) a particular portion of the tissue to be resected or ablated;
      (d) taking a video image after collecting the physical space data; and
      (e) texture mapping the video image onto each registration by a dynamic calibration function.

8. The apparatus according to claim 7, wherein the laser scanner is freely movable and not rigidly fixed during scanning.

9. The apparatus according to claim 8, further comprising:
   (f) an optical tracking system including an optical scanner, the optical tracking system determines triangulated position data of the laser range scanner based on emissions from a plurality of infrared emitting diodes (IREDs) distributed over at least a portion of the laser range scanner, the plurality of IREDs emitting a plurality of intermittent infrared signals used to triangulate the position of the laser range scanner in 3-D image space.

10. An article of manufacture for collecting and processing physical space data for use while performing image-guided surgery, the article of manufacture comprising a computer-readable medium holding computer-executable instructions for performing a method comprising:
    (a) determining registrations used to indicate surgical position in both image space and physical space by processing physical space data collected by (i) illuminating the surface of surgically exposed tissue within a living patient with laser light, (ii) receiving light reflected from the illuminated surface of the exposed tissue within the living patient, and (iii) performing an analysis on the reflected light, the physical space data providing three-dimensional (3-D) coordinates for each of the physical surface points; and
    (b) using the registrations to map into image space,
       (i) image data describing the physical space of an ablative instrument used to perform the image-guided surgery,
       (ii) an ablation zone of the ablative instrument,
       (iii) the tissue, and
       (iv) a particular portion of the tissue to be resected or ablated;
    (c) taking a video image after collecting the physical space data; and
    (d) texture mapping the video image onto each registration by a dynamic calibration function.

11. The article of manufacture of claim 10, wherein the computer-executable instructions perform a method further comprising:
    (e) creating a triangularized mesh based on a 3-D reference of tissue of the patient, the 3-D reference being acquired, stored and processed prior to the tissue being surgically exposed;
    (f) determining the volumetric center of a particular portion of the tissue to be resected or ablated during the surgery; and (g) implementing an algorithm using the triangularized mesh and the physical space data to determine the registrations.

12. The article of manufacture of claim 11, wherein the algorithm is an iterative closest point (ICP) registration algorithm.

13. A method of collecting and processing physical space data for use while performing image-guided surgery, the method comprising:
   (a) surgically exposing tissue within a living patient;
   (b) collecting physical space data by (i) establishing one or more magnetic fields of known shape and size in the proximity of the exposed tissue within the living patient, (ii) acquiring data associated with the strength of the magnetic fields, and (iii) performing an analysis on the acquired data, the physical space data providing three-dimensional (3-D) coordinates for each of a plurality of scanned surface points;
   (c) based on the physical space data collected in step (b), determining registrations used to indicate surgical position in both image space and physical space;
   (d) using the registrations determined in step (c) to map into image space,
       (i) image data describing the physical space of an ablative instrument used to perform the image-guided surgery,
       (ii) an ablation zone of the instrument,
       (iii) the tissue, and
       (iv) a particular portion of the tissue to be resected or ablated; and
   (e) taking a video image after collecting the physical space data; and
   (f) texture mapping the video image onto each registration by a dynamic calibration function.

* * * * *